US006069145A

United States Patent [19]
Betts

[11] Patent Number: 6,069,145
[45] Date of Patent: May 30, 2000

[54] PIPERAZINONEPHENYLOXAZOLIDINONE DERIVATIVES AND THEIR USE AS ANTIBACTERIAL AGENTS

[75] Inventor: Michael John Betts, Macclesfield, United Kingdom

[73] Assignee: Zeneca Limited, London, United Kingdom

[21] Appl. No.: 09/117,337

[22] PCT Filed: Jan. 21, 1997

[86] PCT No.: PCT/GB97/00169

§ 371 Date: Jul. 27, 1998

§ 102(e) Date: Jul. 27, 1998

[87] PCT Pub. No.: WO97/27188

PCT Pub. Date: Jul. 31, 1997

[30] Foreign Application Priority Data

Jan. 27, 1996 [GB] United Kingdom ............... 9601666

[51] Int. Cl.[7] ...................... A61K 31/495; C07D 413/10
[52] U.S. Cl. .......................................... 514/252; 544/369
[58] Field of Search ..................... 544/369, 252

[56] References Cited

U.S. PATENT DOCUMENTS

| | | | |
|---|---|---|---|
| 4,346,102 | 8/1982 | Langlois et al. | 424/279 |
| 4,705,799 | 11/1987 | Gregory | 514/376 |
| 5,164,510 | 11/1992 | Brickner | 548/231 |
| 5,182,403 | 1/1993 | Brickner | 548/231 |
| 5,231,188 | 7/1993 | Brickner | 548/221 |
| 5,523,403 | 6/1996 | Barbachyn | 544/137 |
| 5,529,998 | 6/1996 | Häbich et al. | 514/233.8 |
| 5,652,238 | 7/1997 | Brickner et al. | 514/235.8 |
| 5,792,765 | 8/1998 | Riedl | 514/236.8 |
| 5,827,857 | 10/1998 | Riedl | 514/301 |
| 5,861,413 | 1/1999 | Habich | 514/312 |

FOREIGN PATENT DOCUMENTS

| | | |
|---|---|---|
| 24985/95 | 2/1996 | Australia . |
| 50735/96 | 10/1996 | Australia . |
| 2154024 | 1/1996 | Canada . |
| 127902 | 12/1984 | European Pat. Off. . |
| 184170 | 6/1986 | European Pat. Off. . |
| 312000 | 4/1989 | European Pat. Off. . |
| 609905 | 8/1989 | European Pat. Off. . |
| 352781 | 1/1990 | European Pat. Off. . |
| 359418 | 3/1990 | European Pat. Off. . |
| 657440 | 6/1995 | European Pat. Off. . |
| 693491 | 1/1996 | European Pat. Off. . |
| 694543 | 1/1996 | European Pat. Off. . |
| 694544 | 1/1996 | European Pat. Off. . |
| 697412 | 2/1996 | European Pat. Off. . |
| 738726 | 10/1996 | European Pat. Off. . |
| 2458547 | 1/1981 | France . |
| 2500450 | 8/1982 | France . |
| 195 14 313 | 2/1996 | Germany . |
| 196 01 265 | 6/1997 | Germany . |
| 196 01 264 | 7/1997 | Germany . |
| 196 04 223 | 8/1997 | Germany . |
| 196 49 095 | 8/1997 | Germany . |
| 2028306 | 3/1980 | United Kingdom . |
| 2054575 | 2/1981 | United Kingdom . |
| 2053196 | 4/1981 | United Kingdom . |
| 2094299 | 9/1982 | United Kingdom . |
| 2141716 | 1/1985 | United Kingdom . |
| 93/09103 | 5/1993 | WIPO . |
| 93/23384 | 11/1993 | WIPO . |
| 94/01110 | 1/1994 | WIPO . |
| 94/13649 | 6/1994 | WIPO . |
| 95/07271 | 3/1995 | WIPO . |
| 95/14684 | 6/1995 | WIPO . |
| 95/25106 | 9/1995 | WIPO . |
| 96/13502 | 5/1996 | WIPO . |
| 96/15130 | 5/1996 | WIPO . |
| 96/23788 | 8/1996 | WIPO . |
| 96/35691 | 11/1996 | WIPO . |
| 97/09328 | 3/1997 | WIPO . |
| 97/10223 | 3/1997 | WIPO . |
| 97/10235 | 3/1997 | WIPO . |
| 97/14690 | 4/1997 | WIPO . |
| 97/19089 | 5/1997 | WIPO . |
| 97/21708 | 6/1997 | WIPO . |
| 97/30981 | 8/1997 | WIPO . |
| 97/37980 | 10/1997 | WIPO . |
| 98/07708 | 2/1998 | WIPO . |

OTHER PUBLICATIONS

"Stereochemistry of Carbon Compounds" by Ernest L.Eliel, pp. 47–54, 1962.

Andes et al., Pharmacodynamic Activity of an Oxazolidinone in an Animal Infection Model, Abstract F233, Abstract of the 36th ICACC, 1996, p. 140.

Ashtekar et al., Oxazolidinones, A New Class of Synthetic Antituberculosis Agent, Diagn. Microbiol. Infect. Dis., 1991, 14(6), pp. 465–471.

Barbachyn et al., Identification of a Novel Oxazolidinone (U–100480) with Potent Antimycobacterial Activity., J. Med. Chem., 1996, vol. 39, pp. 680–685.

(List continued on next page.)

*Primary Examiner*—Emily Bernhardt
*Attorney, Agent, or Firm*—Pillsbury Madison & Sutro, LLP

[57] ABSTRACT

The invention concerns a compound of formula (I) wherein: $R^1$ is of the formula —NHC(═O)(1–4C)alkyl, —NHS(O)$_n$(1–4C)alkyl wherein n is 0, 1 or 2 or $R^1$ is hydroxy; $R^2$ and $R^3$ are independently hydrogen or fluoro; $R^4$ is hydrogen, methyl, ethyl or oxo; $R^5$ is hydrogen, (1–6C)alkyl, (2–6C)alkenyl, (2–6C)alkynyl or of the formula $R^6(CH_2)_m$— wherein either m is 1–4 and $R^6$ is, for example, trifluoromethyl, difluoromethyl, fluoromethyl, (1–4C)alkoxy, (1–4C)alkyl S(O)$_p$— wherein p is 0, 1 or 2, (1–6C)alkanoyloxy, di-(N-(1–4C)alkyl)amino, N-((1–4C)alkyl)(1–4C)alkanoylamino, cyano, carboxy, (1–4C)alkoxycarbonyl, carbamoyl, di-(N-(1–4C)alkyl)carbamoyl, N-((1–4C)alkyl)(1–4C)alkanesulphonamido, $N^1$-((1–4C)alkyl)-di-($N^3$-(1–4C)alkyl)ureido, or of the formula —OC(═O)$NR^7(R^8)$ or —N($R^9$)SO$_2$NR$^7$($R^8$) wherein $R^7$ and $R^8$ are independently hydrogen or (1–4C)alkyl and $R^9$ is (1–4C)alkyl; or m is 2–4 and $R^6$ is, for example, hydroxy, (1–4C)alkanoylamino, amino, (1–4C)alkylamino, (1–4C)alkanesulphonamido, ureido, di-($N^3$-(1–4C)alkyl)ureido or of the formula —NHSO$_2$NR$^7$($R^8$); and pharmaceutically-acceptable salts thereof; processes for their preparation; pharmaceutical compositions containing them and their use as antibacterial agents.

10 Claims, No Drawings

OTHER PUBLICATIONS

Barbachyn et al., Synthesis and Antibacterial Activity of New Tropone–Substituted . . . Substitution on In Vivo Activity, Bioorganic & Medical Chemistry Letters, vol. 6, No. 9, 1996, pp. 1009–1014.

Barbachyn et al., Synthesis and Antibacterial Activity of New Tropone–Substituted . . . Tropone Substition Pattern, Bioorganic & Medical Chemistry Letters, vol. 6, No. 9, 1996, pp. 1003–1008.

Barry, In Vitro Evaluation of DuP 105 and DuP 721, Two New Oxazolidinone Antimicrobial Agents, Antimicrobial Agents and Chemotheraphy, Jan. 1988, 32(1), pp. 150–152.

Borthwick et al., 5–(Acetamidomethyl)–3–Aryldihydrofuran–2–Ones, . . . Two New Classes of Antibacterial Agents, Med. Chem. Res., 1996, pp. 22–27.

Brickner et al., Sythesis and Antibacterial Activity of U–100592 . . . Multidrug–Resistant Gram–Positive Bacterial Infections., J. Med. Chem. 1996k vol. 39, 673–679.

Brickner, Oxazolidinone Antibacterial Agents, Current Pharmaceutical Design, 1996, vol. 2, pp. 175–194.

Brumfitt et al., Antibacterial Oxazolidinones In vitro Activity of a New Analogue, E3709, Diagn. Microbiol. Infect. Dis., 1992, vol. 15, pp. 621–625.

Brumfitt et al., In–vitro microbiological activities of DuP 105 and DuP 721, novel synthetic oxazoldinones, Journal of Antimicrobial chemotherapy, 1988, 21(6), pp. 711–720.

Brumfitt et al., Variation in response of Gram–positive cocci to the combination of DuP 721 and ciprofloxacin, J. Anticmicrob. Chemother., 1989, 24(3) pp. 465–466.

Buysse et al. Mutation of the AcrAB Antibiotic Efflux Pump in *Esherichia coli* Confers Susceptibility to Exazolidinone Antibiotics, Abstract C42, Abstract of the 36th ICACC, 1996, p. 41.

Daly et al., Activity and mechanism of action of DuP 105 and DuP 721, new oxaxolidinone compounds, Journal of Antimicrobial Chemotherapy, 1988, 21(6), pp. 721–730.

Denis et al., 5–Aryl–•,• Butenolide, A New Class of Antibacterial Derived . . . N–Aryl Oxazolidinone Dup 721, Bioorganic and Medicinal Chemistry Letters, 1994, vol. 4, No. 16, pp. 1925–1930.

Dostert et al., Structural Modifications in Oxazolidinone Series Leading to Type A or B Selective Monoamine Oxidase Inhibitors, Int. Congress Series. Excerpta Medica, 1982, pp. 197–208.

Eliopoulos et al., In Vitro Activities of New Oxazolidinone Antimicrobial Agents against Enterococci, Antimicrobial Agents and Chemotheraphy, Jul. 1996, 40(7), pp. 1745–1747.

Eustice et al., An Automated Pulse Labelling Method for Structure–Activity Relationship Studies with Antibacterial Oxazolidinones, Durgs. Exptl. Clin. Res., 1990, 16(4), pp. 149–155.

Eustice et al., Mechanism of Action of DuP 721: Inhibition of an Early Event during Initiation of Protein Synthesis, Antimicrobial Agents and Chemotheraphy, Aug, 1988, 32(8), pp. 1218–1222.

Eustice et al., The Mechanism of Action of DuP 721, A New Antibacterial Agent: Effects on Micromolecular Synthesis, Biochem. & Biophys. Res. Commun., Feb. 15, 1988, 150(3), pp. 965–971.

Ford et al., In Vivo Activities of U–100592 and U–100766, . . . against Experimental Bacterial Infections, Antimicrobial Agents and Chemotheraphy, Jun. 1996, 40(6). pp. 1508–1513.

Grega et al., Regioselective Metalation of Fluoroanilines. An Application to the Synthesis of Fluorinated Oxazolidinone Antibacterial Aents; J. Org. Chem., 1995, 60. pp. 5255–5261.

Gregory et al., Antibacterials, Synthesis and Structure–Activity Studies of 3–Aryl–2–oxooxazolidines.1. The "B" Group, J. Med. Chem., 1989, 32(8), pp. 1673–1681.

Gregory et al., Antibacterials. Synthesis and Structure–Activity Studies of 3–Aryl–2–oxooxazolidines.2. The "A" Group, J. Med. Chem., 1990, vol. 33, pp. 2569–2578.

Hutchinson et al., Piperazinyl Oxqzolidinones: Structure Activity Relationships of a New Class of Oxazolidinone Antibacterial Agents, ICAAC (Interscience Congress of Antimicrobial Agents and Chemotherapy) meeting abstracts: Sep. 17–20th 1995, pp. 8–14.

Jones et al., In Vitro Antimicrobial Activities and Spectra of U–100592 and U–100766, . . . Oxazolidinones, Antimicrobial Agents and Chemotheraphy, Mar. 1996, 40(3), pp. 720–726.

Jorgensen et al., In Vitro Activities of the Oxazolidinone Antibiotics U–100592 . . . Negative Staphylococcus Species, Antimicrobial Agents and Chemotheraphy, Feb. 1997, 41(2), pp. 465–467.

Kaatz et al., In Vitro Activities of Oxazolidinone Compounds U100592 . . . *Staphylococcus epidermidis*, Antimicrobial Agents and Chemotheraphy, Mar. 1996, 40(3), pp. 799–801.

Lin et al., Oxazolidiones Block Translation Initiation by Binding to Ribosomes, Abstract C101, Abstract of the 36th ICACC, 1996, p. 52.

Lin et al., The Oxazolidinone Eperezolid Binds to the 50S Ribosomal Subunit . . . of Chloramphenicol and Linocomycin, Antimicrobial Agents and Chemotheraphy, Oct. 1997, 41(10), pp. 2127–2131.

Lizondo et al., Linezolid, Oxazolidinone Antibacterial, Drugs of the Future, 1996, 21(11), pp. 1116–1123.

Lund et al., Hypersegmented Megakaryocytes and Megakaryocytes with Multiple . . . an Oxazolidinone Antibiotic, Toxicologic Pahtyology, 25(4), pp. 339–343.

Maple et al., Comparative in–vitro activity of vancomycin, teicoplanin, . . . methicillin and gentamicin resistant *Staphyloccus aureus*, Journal of Antimicrobial Chemotherapy, 1989, 23(4), pp. 517–525.

Mason et al., In Vitro Activities of Oxazolidinones U–100592 and U–100766 . . . Strains of *Streptocossu pneumoniae*, Antimicrobial Agents and Chemotheraphy, Apr., 1996, 40(4), pp. 1039–1040.

Mini et al., Comparative in Vitro Activity of the New Oxazolidinones DuP 721 and DuP 105 against Staphylococci and Streptococci, Eur. J. Clin. Microbiol. Infect. Dis., 1989, 8(3), pp. 356–360.

Mulazimoglu et al., In Vitro Activities of Two Novel . . . *Staphylococcus aureus* and *Staphylococcus epidermidis*, Antimicrobial Agents and Chemotheraphy, Oct. 1996, 40(10), pp. 2428–2430.

Neu et al., In Vitro Activities of Two Oxazolidinone Antimicrobial Agents, DuP 721 and DuP 105, Antimicrobial Agents and Chemotheraphy, Apr. 1988, 32(4), pp. 580–583.

Park et al., Antibacterials. Synthesis and Structure–Activity Studies of 3–Aryl–2–oxooxazolidines. 4. Multiply–Substituted Aryl Derivatives, J. Med. Chem., 1992, vol. 35, pp. 1156–1165.

Ranaldi et al., Transport of the Antibacterial Agent Oxazolidin–2–One and . . . (MDCK) Epithelial Cell Lines, Antimicrobial Agents and Chemotherphy, Mar. 1996, 40(3), pp. 652–658.

Schaadt et al., Serum Inhibitory Titers and Serum Bactericidal for Human . . . Eperezolid and Linezolid, Diagn. Microbiol. Infect. Dis., 1997, 28(4), pp. 201–204.

Schaus et al., Dynamic Kinetic Resolution . . . Aryl Oxazolidinone Antibacterial Agents, Tetrahedron Letters, 1996, 37(44), pp. 7937–7940.

Scholl et al., Micellar electrokinetic chromatograpny as a generalized alternative . . . of a class of investigational antibacterial drugs., Journal of Chromoatography B, 1997, 695(1), pp. 147–156.

Seneci, et al., Synthesis and Antimicrobial Activity of Oxazolidin–2–ones and Related Heterocycles, J. Chem. Soc. Perkin Trans., 1994, vol. 16, pp. 24352351.

Shinabarger et al., Mechanism of Action of Oxazolidinones: Effects of Linezolid and Eperezolid on Translation Reactions, Antimicrobial Agents and Chemotherapy, Oct. 1997, 41(10), pp. 2132–2136.

Silverman et al., The Oxazlidinone Antibacterial Agent DuP 105 Does not Act on Cell Wall Biosynthesis or on a B–Lactamase, Biochemical and Biophysical Research Communications, Sep. 15, 1993, 195(2), pp. 1077–1080.

Slee et al., Oxazolidinones, A New Class of Synthetic Antibacterial Agents: In Vitro of DuP 105 and DuP 721, Antimicrobial Agents and Chemotheraphy, Nov. 1987, pp. 1791–1797.

Spangler et al., Activities of RPR 106972 (a New Oral Streptogramin), . . . 203 Penicillin–Susceptible and –Resistant Pneumococci, Antimicrobial Agents and Chemotherapy, Feb. 1996, pp. 481–484.

Spangler et al., Activities of RPR 106972 (a New Oral Streptogramin), . . . –Resistant pneumocci, Antimicrobial Agents and Chemotheraphy, Feb. 1996, 40(2), pp. 481–484.

Takagi et al., Safety Pharmacology Evaluation of the Oxazolidinone, U–100766, Abstract 564, Society of Toxicology (SOT) Annual Meeting, 1996, pp. 110.

Wang et al., Chiral Synthesis of Dup 721, A New Antibacterial Agent, Tetrahedron, 1989, 45(5), pp. 1323–1326.

Worth et al., Quality Guidelines for Amoxicillin, . . . Various National Committee for Clinical Laboratory Standards Susceptibility Testing Methods, Diagn. Microbiol. Infect. Dis, 1996, 24(2), pp. 87–91.

Zurenko et al., In Vitro Activities of U–100592 and U–100766, Novel Oxazolidinone Antibacterial Agents, Antimicrobial Agents and Chemotheraphy, Apr. 1996, 40(4), pp. 839–845.

Zurenko et al., Oxazolidinone antibacterial agents: development of the clinical candidates eperezolid and linezolid, Exp. Opin. Invest. Drugs, vol. 6, No. 2, pp. 151–158.

PIPERAZINONEPHENYLOXAZOLIDINONE DERIVATIVES AND THEIR USE AS ANTIBACTERIAL AGENTS

The present invention relates to antibiotic compounds, and in particular to antibiotic compounds containing both piperazinone and oxazolidinone rings. This invention further relates to processes for their preparation, to intermediates useful in their preparation, to their use as therapeutic agents and to pharmaceutical compositions containing them.

The international microbiological community continues to express serious concern that the evolution of antibiotic resistance could result in strains against which currently available antibacterial agents will be ineffective. In general, bacterial pathogens may be classified as either Gram-positive or Gram-negative pathogens. Antibiotic compounds with effective activity against both Gram-positive and Gram-negative pathogens are generally regarded as having a broad spectrum of activity. The compounds of the present invention are regarded primarily as effective against Gram-positive pathogens because of their particularly good activity against such pathogens.

Gram-positive pathogens, for example Staphylococci, Enterococci, Streptococci and mycobacteria, are particularly important because of the development of resistant strains which are both difficult to treat and difficult to eradicate from the hospital environment once established. Examples of such strains are methicillin resistant staphylococcus (MRSA), methicillin resistant coagulase negative staphylococci (MRCNS), penicillin resistant *Streptococcus pneumoniae* and multiply resistant *Enterococcus faecium*.

The major clinically effective antibiotic for treatment of such resistant Gram-positive pathogens is vancomycin. Vancomycin is a glycopeptide and is associated with nephrotoxicity and ototoxicity. Furthermore, and most importantly, antibacterial resistance to vancomycin and other glycopeptides is also appearing. This resistance is increasing at a steady rate rendering these agents less and less effective in the treatment of Gram-positive pathogens.

The present inventors have discovered a class of antibiotic compounds containing an oxazolidinone ring which has useful activity against Gram-positive pathogens including MRSA and MRCNS and, in particular, against various strains exhibiting resistance to vancomycin and against *E. faecium* strains resistant to both aminoglycosides and clinically used β-lactams.

We have now discovered a narrow range of compounds that is not suggested by the art and which has good activity against a broad range of Gram-positive pathogens including organisms known to be resistant to most commonly used antibiotics. In comparison with compounds described in the art (for example Walter A. Gregory et al in J.Med.Chem. 1990, 33, 2569–2578 and Chung-Ho Park et al in J.Med.Chem. 1992, 35, 1156–1165) the compounds also possess a favourable toxicological profile.

Accordingly, the present invention provides a compound of the formula (I):

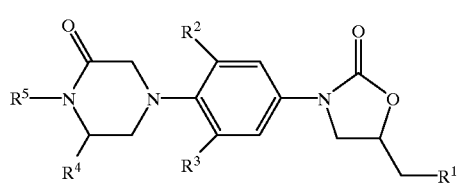

wherein:
$R^1$ is of the formula —NHR(=O)(1–4C)alkyl, —NHS(O)$_n$(1–4C)alkyl wherein n is 0, 1 or 2 or $R^1$ is hydroxy;

$R^2$ and $R^3$ are independently hydrogen or fluoro;
$R^4$ is hydrogen, methyl, ethyl or oxo;
$R^5$ is hydrogen, (1–6C)alkyl, (2–6C)alkenyl, (2–6C)alkynyl or of the formula $R^6(CH_2)_m$— wherein either m is 1–4 and $R^6$ is trifluoromethyl, difluoromethyl, fluoromethyl, (1–4C)alkoxy, (1–4C)alkyl S(O)$_p$— wherein p is 0, 1 or 2, (1–6C)alkanoyloxy, di-(N-(1–4C)alkyl)amino, N-((1–4C)alkyl)(1–4C)alkanoylamino, cyano, carboxy, (1–4C)alkoxycarbonyl, carbamoyl, N-(1–4C)alkylcarbamoyl, di-(N-(1–4C)alkyl)carbamoyl, N-((1–4C)alkyl)(1–4C)alkanesulphonamido, $N^1$-((1–4C)alkyl)ureido, $N^1$-((1–4C)alkyl)-$N^3$-((1–4C)alkyl)ureido, $N^1$-((1–4C)alkyl)-di-($N^3$-(1–4C)alkyl)ureido, or of the formula —OC(=O)NR$^7$(R$^8$) wherein R$^7$ and R$^8$ are independently hydrogen or (1–4C)alkyl or of the formula —N(R$^9$)SO$_2$NR$^7$(R$^8$) wherein R$^7$ and R$^8$ are as hereinabove defined and R$^9$ is (1–4C)alkyl;

or m is 2–4 and R$^6$ is hydroxy, (1–4C)alkanoylamino, amino, (1–4C)alkylamino, (1–4C)alkanesulphonamido, ureido, $N^3$-((1–4C)alkyl)ureido, di-($N^3$-(1–4C)alkyl)ureido or of the formula —NHSO$_2$NR$^7$(R$^8$) wherein R$^7$ and R$^8$ are as hereinabove defined;

and pharmaceutically-acceptable salts thereof.

In this specification the generic term "alkyl" includes straight chained and branched structures, for example (1–6C)alkyl includes propyl, isopropyl and tert-butyl. However, references to individual alkyl groups such as "propyl" are specific for the straight-chain version only, and references to individual branched-chain alkyl groups such as "isopropyl" are specific for branched-chain versions only. An analogous convention applies to other generic terms.

Examples of (1–4C)alkyl and (1–6C)alkyl include methyl, ethyl, propyl, isopropyl and tert-butyl; examples of N-(1–4C)alkylcarbamoyl include methylcarbamoyl and ethylcarbamoyl; examples of di(N-(1–4C)alkyl)carbamoyl include di(methyl)carbamoyl and di(ethyl)carbamoyl; examples of (1–6C)alkylS(O)p— include methylthio, ethylthio, methylsulphinyl, ethylsulphinyl, methylsulphonyl and ethylsulphonyl; examples of (2–6C)alkenyl include allyl and vinyl; examples of (2–6C)alkynyl include ethynyl and 2-propynyl; examples of (1–4C)alkoxy include methoxy, ethoxy and propoxy; examples of (1–6C)alkanoylamino include acetamido and propionylamino; examples of N-((1–4C)alkyl)(1–4C)alkanoylamino include N-methylacetamido, N-methylpropionylamino and N-ethylacetamido; examples of (1–6C)alkanesulphonamido include methanesulphonamido and ethanesulphonamido; examples of N-((1–4C)alkyl)-1–4C)alkanesulphonamido include N-(methyl)-methanesulphonamido, N-(methyl)ethanesulphonamido and N-(ethyl)ethanesulphonamido; examples of (1–4C)alkanoyloxy include acetyloxy and propionyloxy; examples of N-(1–4C)alkylamino include methylamino and ethylamino; examples of di-(N-(1–4C)alkyl)amino include di-N-methylamino, di-(N-ethyl)amino and N-ethyl-N-methylamino; examples of (1–4C)alkoxycarbonyl include methoxycarbonyl and ethoxycarbonyl; examples of $N^2$-((1–4C)alkyl)ureido include $N^1$-methylureido and $N^1$-ethylureido; examples of $N^1$-((1–4C)alkyl-$N^3$-((1–4C)alkyl)ureido include $N^1$-methyl-N3-methylureido, $N^1$-ethyl-$N^3$-methylureido and $N^1$-ethyl-$N^3$-ethylureido; examples of $N^1$-((1–4C)alkyl)-di-($N^3$-(1–4C)alkyl)ureido include $N^1$-methyl-di-($N^3$-methyl)ureido, $N^1$-ethyl-di-($N^3$-methyl)ureido and $N^1$-methyl-$N^3$-ethyl-$N^3$-methylureido; examples of $N^3$-((1–4C)alkyl)ureido include $N^3$-methylureido, and $N^3$-ethylureido; and examples of di-($N^3$-(1–4C)alkyl)ureido include di-($N^3$-methyl)ureido, $N^3$-ethyl-$N^3$-methylureido and di-($N^3$-ethyl)ureido.

The compounds of the present invention have a chiral centre at the C5-position. The pharmaceutically active enantiomer is of the formula (IA):

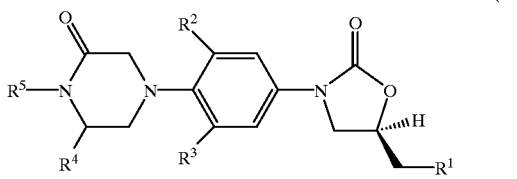

(IA)

The present invention includes the pure enantiomer or disastereoisomer depicted above and mixtures of the 5(R) and 5(S) enantiomers or diastereoisomers, for example a racemic mixture or equal mixtures of diastereoisomers. If a mixture of 5(R) and 5(S) is used, a larger amount (depending up on the ratio of the enantiomers or diastereoisomers) will be required to achieve the same effect as the same weight of the pharmaceutically active enantiomer.

Furthermore, some compounds of the formula (I) may have other chiral centres.

It is to be understood that certain compounds of the formula I can exist in solvated as well as unsolvated form such as, for example, hydrated forms. It is to be understood that the invention encompasses all such solvated forms which possess antibacterial activity.

Suitable pharmaceutically-acceptable salts include acid addition salts such as hydrochloride, hydrobromide, citrate, maleate, methanesulfonate, fumarate and salts formed with phosphoric and sulfuric acid. In another aspect suitable salts are base salts such as sodium, an alkaline earth metal salt for example calcium or magnesium, an ammonium or tetra-(2-hydroxyethyl)ammonium salt, an organic amide salt for example triethylamine, morpholine, N-methylpiperidine, N-ethylpiperidine, procaine, dibenxylamine, N,N-dibenzylethylamine or amino acids for example lysine. There may be more than one cation or anion depending on the number of charged functions and the valency of the cations or anions. A preferred pharmaceutically-acceptable salt is the sodium salt.

However, to facilitate isolation of the salt during preparation, salts which are less soluble in the chosen solvent may be preferred whether pharmaceutically-acceptable or not.

The compounds of the formula (I) may be administered in the form of a pro-drug which is broken down in the human or animal body to give a compound of the formula (I). Examples of pro-drugs include in-vivo hydrolysable esters of a compound of the formula (I).

An in-vivo hydrolysable ester of a compound of the formula (I) containing carboxy or hydroxy group is, for example, a pharmaceutically-acceptable ester which is hydrolysed in the human or animal body to produce the parent acid or alcohol. Suitable pharmaceutically-acceptable esters for carboxy include (1–6C)alkoxymethyl esters, for example methoxymethyl; (1–6C)alkanoyloxymethyl esters, for example pivoloyloxymethyl; phthalidyl esters; (3–8C) cycloalkylcarbonyloxy-(1–6C)alkyl esters, for example 1-cyclohexylcarbonyloxyethyl; 1,3-dioxolen-2-onylmethyl esters, for example 5-methyl-1,3-dioxolen-2-onylmethyl; and (1–6C)alkoxycarbonyloxyethyl esters, for example 1-methoxycarbonyloxyethyl; and may be formed at any carboxy group in the compounds of this invention.

An in-vivo hydrolysable ester of a compound of the formula (I) containing a hydroxy group is, for example, a pharmaceutically-acceptable ester which is hydrolysed in the human or animal body to produce the parent alcohol. The term includes inorganic esters such as phosphate esters and α-acyloxyalkyl ethers and related compounds which as a result of the in-vivo hydrolysis of the ester breakdown to give the parent hydroxy group. Examples of α-acyloxyalkyl ethers include acetoxymethoxy and 2,2-dimethylpropionyloxymethoxy. A selection of in-vivo hydrolysable ester forming groups for hydroxy include alkanoyl, benzoyl, phenylacetyl, and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl.

Preferred compounds of the invention comprise a compound of the formula (I), or a pharmaceutically-acceptable salt thereof, wherein the substituents $R^1$ to $R^9$ have the values disclosed hereinbefore or have any of the following values:

a) Preferably $R^1$ is of the formula —NHC(=O)(1–4C)alkyl.
b) Most preferably $R^1$ is acetamido.
c) In another aspect $R^1$ is hydroxy.
d) Preferably one of $R^2$ and $R^3$ is hydrogen and the other is fluoro.
e) Preferably $R^4$ is hydrogen, methyl or oxo.
f) More preferably $R^4$ is hydrogen or oxo.
g) Most preferably $R^4$ is hydrogen.
h) Preferably $R^5$ is (1–6C)alkyl or of the formula $R^6(CH_2)_m$— wherein either m is 1 or 2 and $R^6$ is trifluoromethyl, (1–4C)alkoxy, (1–4C)alkylS(O)$_p$— (wherein p is 0, 1 or 2), (1–4C)alkoxycarbonyl, carbamoyl, N-(1–4C)alkylcarbamoyl, or di-(N-(1–4C)alkyl)carbamoyl, or m is 2 or 3 and $R^6$ is hydroxy or (1–4C)alkanoylamino.
i) More preferably, $R^5$ is methyl, ethyl, 2,2,2-trifluoroethyl, 2-methoxyethyl, methylthiomethyl, methoxycarbonylmethyl, carbamoylmethyl, di-(N-methyl)carbamoylmethyl, 2-hydroxyethyl or 2-(acetamido)ethyl.
j) Most preferably $R^5$ is 2-fluoroethyl.

Therefore, in another aspect of the invention preferred compounds of the invention comprise a compound of the formula (I) wherein:
a) $R^1$ is of the formula —NHC(=O)(1–4C)alkyl; $R^2$ and $R^3$ is hydrogen and the other is fluoro; $R^4$ is hydrogen, methyl or oxo; $R^5$ is (1–6C)alkyl or of the formula $R^6(CH_2)_m$— wherein either m is 1 or 2 and $R^6$ is trifluoromethyl, (1–4C)alkoxy, (1–4C)alkylS(O)$_p$— (wherein p is 0, 1 or 2), (1–4C)alkoxycarbonyl, carbamoyl, N-(1–4C)alkylcarbamoyl, or di-(N-(1–4C)alkyl)carbamoyl, or m is 2 or 3 and $R^6$ is hydroxy or (1–4C)alkanoylamino.
b) $R^1$ is of the formula —NHC(=O)(1–4C)alkyl; $R^2$ and $R^3$ is hydrogen and the other is fluoro; $R^4$ is hydrogen, methyl or oxo; $R^5$ is (1–6C)alkyl or of the formula $R^6(CH_2)_m$— wherein either m is 1 or 2 and $R^6$ is trifluoromethyl, fluoromethyl, (1–4C)alkoxy, (1–4C)alkylS(O)$_p$— (wherein p is 0, 1 or 2), (1–4C)alkoxycarbonyl, carbamoyl, N-(1–4C)alkylcarbamoyl, or di-(N-(1–4C)alkyl)carbamoyl, or m is 2 or 3 and $R^6$ is hydroxy or (1–4C)alkanoylamino.
c) $R^1$ is acetamido; $R^2$ and $R^3$ is hydrogen and the other is fluoro; $R^4$ is hydrogen, methyl or oxo; $R^5$ is (1–6C)alkyl or of the formula $R^6(CH_2)_m$— wherein either m is 1 or 2 and $R^6$ is trifluoromethyl, (1–4C)alkoxy, (1–4C)alkylS(O)$_p$— (wherein p is 0, 1 or 2), (1–4C)alkoxycarbonyl, carbamoyl, N-(1–4C)alkylcarbamoyl, or di-(N-(1–4C)alkyl)carbamoyl, or m is 2 or 3 and $R^6$ is hydroxy or (1–4C)alkanoylamino.
d) $R^1$ is acetamido; $R^2$ and $R^3$ is hydrogen and the other is fluoro; $R^4$ is hydrogen, methyl or oxo; $R^5$ is (1–6C)alkyl or of the formula $R^6(CH_2)_m$— wherein either m is 1 or 2 and $R^6$ is trifluoromethyl, fluoromethyl, (1–4C)alkoxy, (1–4C)alkylS(O)$_p$— (wherein p is 0, 1 or 2), (1–4C)alkoxycarbonyl, carbamoyl, N-(1–4C)alkylcarbamoyl, or di-(N-(1–4C)alkyl)carbamoyl, or m is 2 or 3 and $R^6$ is hydroxy or (1–4C)alkanoylamino.

e) $R^1$ is hydroxy; $R^2$ and $R^3$ is hydrogen and the other is fluoro; $R^4$ is hydrogen, methyl or oxo; $R^5$ is (1–6C)alkyl or of the formula $R^6(CH_2)_m$— wherein either m is 1 or 2 and $R^6$ is trifluoromethyl, (1–4C)alkoxy, (1–4C)alkylS(O)$_p$— (wherein p is 0, 1 or 2), (1–4C)alkoxycarbonyl, carbamoyl, N-(1–4C)alkylcarbamoyl, or di-(N-(1–4C)alkyl)carbamoyl, or m is 2 or 3 and $R^6$ is hydroxy or (1–4C)alkanoylamino.

f) $R^1$ is hydroxy; $R^2$ and $R^3$ is hydrogen and the other is fluoro; $R^4$ is hydrogen, methyl or oxo; $R^5$ is (1–6C)alkyl or of the formula $R^6(CH_2)_m$— wherein either m is 1 or 2 and $R^6$ is trifluoromethyl, fluoromethyl, (1–4C)alkoxy, (1–4C)alkylS(O)$_p$— (wherein p is 0, 1 or 2), (1–4C)alkoxycarbonyl, carbamoyl, N-(1–4C)alkylcarbamoyl, or di-(N-(1–4C)alkyl)carbamoyl, or m is 2 or 3 and $R^6$ is hydroxy or (1–4C)alkanoylamino.

g) $R^1$ is acetamido; $R^2$ and $R^3$ is hydrogen and the other is fluoro; $R^4$ is hydrogen, methyl or oxo; $R^5$ is (1–6C)alkyl or of the formula $R^6(CH_2)_m$— wherein either m is 1 or 2 and $R^6$ is trifluoromethyl, (1–4C)alkoxy, (1–4C)alkylS(O)$_p$— (wherein p is 0, 1 or 2), (1–4C)alkoxycarbonyl, carbamoyl, N-(1–4C)alkylcarbamoyl, or di-(N-(1–4C)alkyl)carbamoyl, or m is 2 or 3 and $R^6$ is hydroxy or (1–4C)alkanoylamino.

h) $R^1$ is acetamido; $R^2$ and $R^3$ is hydrogen and the other is fluoro; $R^4$ is hydrogen or oxo; $R^5$ is (1–6C)alkyl or of the formula $R^6(CH_2)_m$— wherein either m is 1 or 2 and $R^6$ is trifluoromethyl, fluoromethyl, (1–4C)alkoxy, (1–4C)alkylS(O)$_p$— (wherein p is 0, 1 or 2), (1–4C)alkoxycarbonyl, carbamoyl, N-(1–4C)alkylcarbamoyl, or di-(N-(1–4C)alkyl) carbamoyl, or m is 2 or 3 and $R^6$ is hydroxy or (1–4C) alkanoylamino.

i) $R^1$ is acetamido; $R^2$ and $R^3$ is hydrogen and the other is fluoro; $R^4$ is hydrogen; $R^5$ is (1–6C)alkyl or of the formula $R^6(CH_2)_m$— wherein either m is 1 or 2 and $R^6$ is trifluoromethyl, (1–4C)alkoxy, (1–4C)alkylS(O)$_p$— (wherein p is 0, 1 or 2), (1–4C)alkoxycarbonyl, carbamoyl, N-(1–4C)alkylcarbamoyl, or di-(N-(1–4C)alkyl)carbamoyl, or m is 2 or 3 and $R^6$ is hydroxy or (1–4C)alkanoylamino.

j) $R^1$ is acetamido; $R^2$ and $R^3$ is hydrogen and the other is fluoro; $R^4$ is hydrogen; $R^5$ is (1–6C)alkyl or of the formula $R^6(CH_2)_m$— wherein either m is 1 or 2 and $R^6$ is trifluoromethyl, fluoromethyl, (1–4C)alkoxy, (1–4C)alkylS(O)$_p$— (wherein p is 0, 1 or 2), (1–4C)alkoxycarbonyl, carbamoyl, N-(1–4C)alkylcarbamoyl, or di-(N-(1–4C)alkyl) carbamoyl, or m is 2 or 3 and $R^6$ is hydroxy or (1–4C) alkanoylamino.

k) $R^1$ is acetamido; $R^2$ and $R^3$ is hydrogen and the other is fluoro; $R^4$ is hydrogen; $R^5$ is methyl, ethyl, 2,2,2-trifluoroethyl, 2-methoxyethyl, methylthiomethyl, methoxycarbonylmethyl, carbamoylmethyl, di-(N-methyl) carbamoylmethyl, 2-hydroxyethyl or 2-(acetamido)ethyl).

l) $R^1$ is acetamido; $R^2$ and $R^3$ is hydrogen and the other is fluoro; $R^4$ is hydrogen; $R^5$ is methyl, ethyl, 2,2,2-trifluoroethyl, 2-fluoroethyl, 2-methoxyethyl, methylthiomethyl, methoxycarbonylmethyl, carbamoylmethyl, di-(N-methyl)carbamoylmethyl, 2-hydroxyethyl or 2-(acetamido)ethyl).

Particular compounds of the present invention are:
N-((5S)-3-(3-fluoro-4-(4-methyl-3-oxopiperazin-1-yl) phenyl)-2-oxooxazolidin-5-yl)methyl)acetamide;
N-((5S)-3-(3-fluoro-4-(4-ethyl-3-oxopiperazin-1-yl) phenyl)-2-oxooxazolidin-5-ylmethyl)acetamide;
N-((5S)-3-(3-fluoro-4-(4-(2,2,2-trifluoroethyl)-3-oxopiperazin-1-yl)phenyl)-2-oxooxazolidin-5-ylmethyl) acetamide;
N-((5S)-3-(3-fluoro-4-(4-(2-fluoroethyl)-3-oxopiperazin-1-yl)phenyl)-2-oxooxazolidin-5-ylmethyl)acetamide;
N-((5S)-3-(3-fluoro-4-(4-(2-hydroxyethyl)-3-oxopiperazin-1-yl)phenyl)-2-oxooxazolidin-5-ylmethyl)acetamide;
N-((5S)-3-(3-fluoro-4-(4-(2-methoxyethyl)-3-oxopiperazin-1-yl)phenyl)-2-oxooxazolidin-5-ylmethyl)acetamide;
N-((5S)-3-(3-fluoro-4-(4-methoxycarbonylmethyl-3-oxopiperazin-1-yl)phenyl)-2-oxooxazolidin-5-ylmethyl) acetamide;
N-((5S)-3-(3-fluoro-4-(4-carbamoylmethyl-3-oxopiperazin-1-yl)phenyl)-2-oxooxazolidin-5-ylmethyl)acetamide;
N-((5S)-3-(3-fluoro-4-(4-N,N-dimethylcarbamoylmethyl-3-oxopiperazin-1-yl)phenyl)-2-oxooxazolidin-5-ylmethyl) acetamide;
N-((5S)-3-(3-fluoro-4-(4-(2-acetamidoethyl)-3-oxopiperazin-1-yl)phenyl)-2-oxooxazolidin-5-ylmethyl) acetamide; or pharmaceutically-acceptable salts thereof.

Particular preferred compounds of the invention are:
N-((5S)-3-(3-fluoro-4-(4-methyl-3-oxopiperazin-1-yl) phenyl)-2-oxooxazolidin-5-yl)methyl)acetamide;
N-((5S)-3-(3-fluoro-4-(4-ethyl-3-oxopiperazin-1-yl) phenyl)-2-oxooxazolidin-5-ylmethyl)acetamide;
N-((5S)-3-(3-fluoro-4-(4-(2-fluoroethyl)-3-oxopiperazin-1-yl)phenyl)-2-oxooxazolidin-5-ylmethyl)acetamide;
N-((5S)-3-(3-fluoro-4-(4-(2-methoxyethyl)-3-oxopiperazin-1-yl)phenyl)-2-oxooxazolidin-5-ylmethyl)acetamide; or pharmaceutically-acceptable salts thereof.

An especially preferred compound of the invention is:
N-((5S)-3-(3-fluoro-4-(4-(2-fluoroethyl)-3-oxopiperazin-1-yl)phenyl)-2-oxooxazolidin-5-ylmethyl)acetamide; or pharmaceutically-acceptable salts thereof.

In a further aspect the present invention provides a process for preparing a compound of the formula (I) or a pharmaceutically-acceptable salt thereof. The compounds of the formula (I) may be prepared by deprotecting a compound of the formula (II):

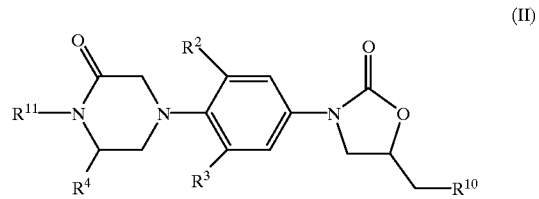

(II)

wherein $R^2$–$R^4$ are as hereinabove defined, $R^{10}$ is $R^1$ or protected $R^1$ and $R^{11}$ is $R^5$ or protected $R^5$, and thereafter, if necessary, forming a pharmaceutically-acceptable salt.

Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Specific examples of protecting groups are given below for the sake of convenience, in which "lower" signifies that the group to which it is applied preferably has 1–4 carbon atoms. It will be understood that these examples are not exhaustive. Where specific examples of methods for the removal of protecting groups are given below these are similarly not exhaustive. The use of protecting groups and methods of deprotection not specifically mentioned is of course within the scope of the invention.

A carboxy protecting group may be the residue of an ester-forming aliphatic or araliphatic alcohol or of an ester-forming silanol (the said alcohol or silanol preferably containing 1–20 carbon atoms).

Examples of carboxy protecting groups include straight or branched chain (1–12C)alkyl groups (eg isopropyl, tert-butyl); lower alkoxy lower alkyl groups (eg methoxymethyl, ethoxymethyl, isobutoxymethyl; lower aliphatic acyloxy lower alkyl groups, (eg acetoxymethyl, propionyloxymethyl, butyryloxymethyl, pivaloyloxymethyl); lower alkoxycarbonyloxy lower alkyl groups (eg 1-methoxycarbonyloxyethyl, 1-ethoxycarbonyloxyethyl); aryl lower alkyl groups (eg p-methoxybenzyl, o-nitrobenzyl, p-nitrobenzyl, benzhydryl and phthalidyl); tri(lower alkyl)silyl groups (eg trimethylsilyl and tert-butyldimethylsilyl); tri(lower alkyl)silyl lower alkyl groups (eg trimethylsilylethyl); and (2–6C)alkenyl groups (eg allyl and vinylethyl).

Methods particularly appropriate for the removal of carboxyl protecting groups include for example acid-, metal- or enzymically-catalysed hydrolysis.

Examples of hydroxy protecting groups include lower alkenyl groups (eg allyl); lower alkanoyl groups (eg acetyl); lower alkoxycarbonyl groups (eg tert-butoxycarbonyl); lower alkenyloxycarbonyl groups (eg allyloxycarbonyl); aryl lower akloxycarbonyl groups (eg benzoyloxycarbonyl, p-methoxybenzyloxycarbonyl, o-nitrobenzyloxycarbonyl, p-nitrobenzyloxycarbonyl); tri lower alkyl/arylsily groups (eg trimethylsily, tert-butyldimethylsilyl, tert-butyldiphenylsilyl); aryl lower alkyl groups (eg benzyl) groups; and triaryl lower alkyl groups (eg triphenylmethyl).

Examples of amino protecting groups include formyl aralkyl groups (eg benzyl and substituted benzyl, eg p-methoxybenzyl, nitrobenzyl and 2,4-dimethoxybenzyl, and triphenylmethyl); di-p-anisylmethyl and furylmethyl groups; lower alkoxycarbonyl (eg tert-butoxycarbonyl); lower alkenyloxycarbonyl (eg allyloxycarbonyl); aryl lower alkoxycarbonyl groups (eg benzyloxycarbonyl, p-methoxybenzyloxycarbonyl, o-nitrobenzyloxycarbonyl, p-nitrobenzyloxycarbonyl; trialkysilyl (eg trimethylsilyl and tert-butylsimethylsilyl); alkylidene (eg methylidene); benzylidene and substituted benzylidene groups.

Methods appropriate for removal of hydroxy and amino protecting groups include, for example, acid-, metal- or enzymically-catalysed hydrolysis, for groups such as o-nitrobenzyloxycarbonyl, photolysis and for groups such as silyl groups, fluoride.

Examples of protecting groups for amide groups include aralkoxymethyl (eg. benzyloxymethyl and substituted benzyloxymethyl); alkoxymethyl (eg. methoxymethyl and trimethylsilylethoxymethyl); trialkyl/arylsilyl (eg. trimethylsilyl, t-butyldimethylsilyl, tert-butyldiphenylsilyl); tri alkyl/arylsilyloxymethyl (eg. tert-butyldimethylsilyloxymethyl, tert-butyldiphenylsilyloxymethyl); 4-alkoxyphenyl (eg. 4-methoxyphenyl); 2,4-di(alkoxy)phenyl (eg. 2,4-dimethoxyphenyl); 4-alkoxybenzyl (eg. 4-methoxybenzyl); 2,4-di(alkoxy)benzyl (eg. 2,4-di(methoxy)benzyl); and alk-1-enyl (eg. allyl, but-1-enyl and substituted vinyl eg. 2-phenylvinyl).

Aralkoxymethyl, groups may be introduced onto the amide group by reacting the latter group with the appropriate aralkoxymethyl chloride, and removed by catalytic hydrogenation. Alkoxymethyl, tri alkyl/arylsilyl and tri alkyl/silyl groups may be introduced by reacting the amide with the appropriate chloride and removing with acid, or in the case of the silyl containing groups fluoride ions. The alkoxyphenyl and alkoxybenzyl groups are conveniently introduced by arylation or alkylation with an appropriate halide and removed by oxidation with ceric ammonium nitrate. Finally alk-1-enyl groups may be introduced by reacting the amide with the appropriate aldehyde and removed with acid.

For further examples of protecting groups see one of the many general texts on the subject, for example, 'Protective Groups in Organic Synthesis' by Theodora Green (publisher: John Wiley & Sons).

In another aspect of the present invention the compounds of the formulae (I) and (II) and pharmaceutically-acceptable salts thereof can be prepared:
a) by modifying a substituent in, or introducing a substituent into, another compound of the formula (I);
b) when $R^1$ is of the formula —NHS(O)$_n$(1–4C)alkyl, wherein n is 1 or 2, by oxidising a compound of the formula (I) wherein n is 0 or, when n is 2 by oxidising a compound of the formula (I) wherein n is 1;
c) when $R^1$ is of the formula —NHC(=O)(1–4C)alkyl or —NHS(O)$_n$(1–4C)alkyl, by reacting a compound of the formula (III) with a compound of the formula (IV):

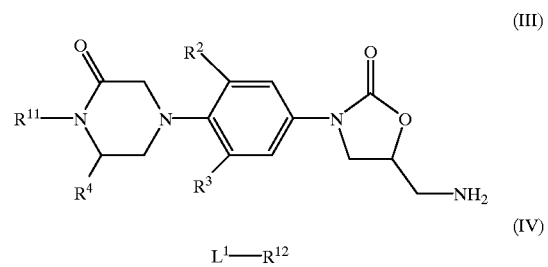

(III)

(IV)

d) when $R^1$ is hydroxy, by reacting a compound of the formula (V) with a compound of the formula (VI):

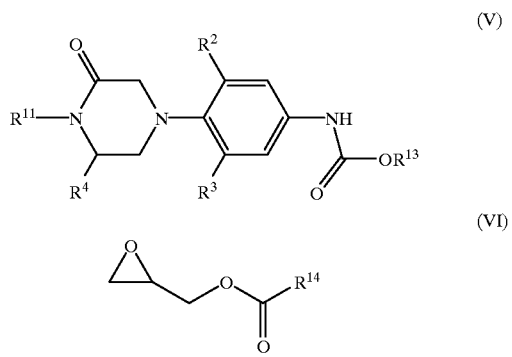

(V)

(VI)

e) when $R^1$ or $R^{10}$ is of the formula —NHC(=O)(1–4C) alkyl, the reaction of a compound of the formula (I) or (II) wherein $R^1$ or $R^{10}$ is hydroxy, with an amide of the formula (VII):

(VII)

wherein $R^2$–$R^4$, $R^{10}$ and $R^{11}$ are as hereinabove defined, $R^{12}$ is of the formula —C(=O)(1–4C)alkyl or —S(O)$_n$(1–4C)alkyl,
$R^{13}$ is (1–6C)alkyl or benzyl, $R^{14}$ is (1–6C)alkyl and $L^1$ is a leaving group;
and thereafter is necessary:
  i) removing any protecting groups;
  forming a pharmaceutically-acceptable salt.
Methods for converting substituents into other substituents are known in the art. For example an alkylthio group may be oxidised to an alkylsulphinyl or alkysulphonyl group, a cyano group reduced to an amino group, a nitro group reduced to an amino group, a hydroxy group alkylated to a methoxy group, or a bromo group converted to an alkylthio group.

Compounds of the formula (I) or (II) wherein $R^1$ or $R^{10}$ is —NHS(O)$_n$(1–4C)alkyl can be prepared by oxidising a compound of the formula (I) or (II) with standard reagents known in the art for the oxidation of a thio group to a sulphinyl or sulphonyl group. For example, a thio group may be oxidised to a sulphinyl group with a peracid such as m-chloroperoxybenzoic acid and oxidising agents such as potassium permanganate will convert a thio group to a sulphonyl group. Compounds of the formula (I) or (II) wherein $R^1$ or $R^{10}$ is —NHS(1–4C)alkyl can be prepared by reacting compounds of the formula (III) with a reagent such as (1–4C)alkylSCl.

Standard reaction conditions for the acetylation of an amine group in a compound of the formula (III) or its conversion to a sulphonamido group are known in the art. For example, the amino group can be acetylated to give an acetamido group using the Schotten-Baumann procedure; reacting the compound of the formula (III) with acetic anhydride in aqueous sodium hydroxide and THF in a temperature range of 0° to 60° C., preferably between 0° C. and ambient temperature. Preferably the acylation is carried out in situ following the catalytic hydrogenation of a compound of the formula (IIIA) (below), by performing the hydrogenation in the presence of acetic anhydride.

A compound of the formula (III) could for example be converted to a compound of the formula (I) or (II) wherein $R^1$ or $R^{10}$ is (1–4C)SO$_2$NH— by reacting the compound of the formula (III) with a sulphonyl chloride. For example, by reacting the compound of the formula (III) with mesyl chloride in a mild base such as pyridine.

Alternatively compounds of the formula (I) or (II) wherein $R^1$ or $R^{10}$ is (1–4C)alkylSO$_2$NH— or (1–4C)alkylSONH— may be prepared by reacting a compound of the formula (III) with a compound of the formula (IV) wherein $L^1$ is a phthalimido group, or preferably $L^1$ is halo, for example chloro.

The compound of the formula (IV) wherein $L^1$ is phthalimido may be prepared by oxidising a compound of the formula (IVA):

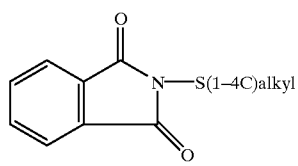

(IVA)

with standard oxidising agents known for the conversion of a thio group to a sulphinyl or sulphonyl group. Compounds of the formula (IVA) can be prepared by reacting phthalimide with an alkylthiohalide, preferably the alkylthiochloride ((1–4C)alkylSCl).

A compound of the formula (III) may be prepared by reducing a compound of the formula (IIIA):

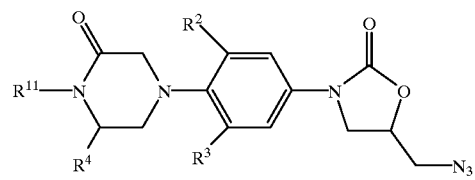

(IIIA)

wherein $R^2$–$R^4$ and $R^{11}$ are as hereinabove defined.

Suitable reducing agents include triethylamine/hydrogen sulphide, triphenylphosphine or phosphite ester, or hydrogen in the presence of a catalyst. More specifically a compound of the formula (IIIA) may be converted to a compound of the formula (III) by heating it in an aprotic solvent, such as 1,2-dimethoxyethane, in the presence of P(OMe)$_3$ and subsequently heating in 6N aqueous hydrochloric acid, or reacting it with hydrogen in the presence of palladium on carbon in an aprotic solvent such as DMF or ethyl acetate. For further details on the reduction of azides to amines see U.S. Pat. No. 4,705,799. A compound of the formula (IIIA) may be reduced and converted to a compound of the formula (I) or (II) in situ using acetic anhydride in DMF.

A compound of the formula (IIIA) maybe prepared by reacting a compound of the formula (IIIB):

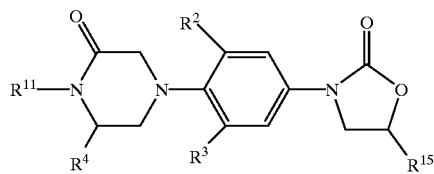

(IIIB)

wherein $R^{15}$ is mesyloxy or tosyloxy, with a source of azide. For example, by reacting (IIIB) with sodium azide in an inert solvent such as DMF in a temperature range of ambient to 100° C., normally in the region of 75° C.–85° C. A compound of the formula (IIIB) may be prepared by converting the hydroxy group in a compound of the formula (I) or (II) wherein $R^1$ or $R^{10}$ is hydroxy into a tosyloxy or mesyloxy group by standard methods known in the art. For example, by reacting said hydroxy compound of the formula (I) or (II) with tosyl chloride or mesyl chloride in the presence of a mild base such as triethylamine.

Alternatively, a compound of the formula (III) may be prepared using similar processes to those used hereinabove and hereinafter for the preparation of compounds of the formulae (I) and (II).

Compounds of the formulae (V) and (VI) are conveniently reacted together in the presence of a strong base such as butyl lithium, lithium hexamethyldisilazide, lithium tert-butoxide, or lithium diisopropylamide. The reaction is conveniently carried out in an inert solvent such as tetrahydrofuran (THF), dimethylformamide (DMF), $\underline{N},\underline{N}^1$-dimethylpropyleneurea (DMPU) or $\underline{N}$-methylpyrrolidone in a temperature range of −78° C. to −50° C. for the deprotonation and cyclisation. Suitable values for $R^{13}$ include ethyl and benzyl and suitable values for $R^{14}$ include ethyl and n-propyl, preferably n-propyl.

A compound of the formula (V) is conveniently prepared by reacting a chloroformate of the formula (ClCOOR$^{13}$) with a compound of the formula (VA):

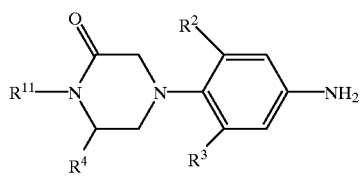

(VA)

wherein $R^2$–$R^4$ and $R^{11}$ are as hereinabove defined. The reaction is conveniently carried out in the presence of an inorganic or organic base such as sodium bicarbonate or an amine base such as dimethylaniline, the former in a solvent such as acetone/water and the latter in an organic solvent such as THF, toluene, DMF or acetonitrile.

A compound of the formula (VA) may be prepared by reducing a compound of the formula (VB):

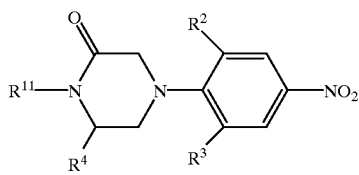

(VB)

wherein $R^2$–$R^4$ and $R^{11}$ are as hereinabove defined.

Many reduction methods suitable for the reduction of a nitro to an amino group are known in the art, for example catalytic hydrogenation and metal reductions. Suitable catalysts in catalytic hydrogenation include Raney nickel, platinum metal and its oxide, rhodium, palladium-on-charcoal and Wilkinson's catalyst RhCl (Ph$_3$P)$_3$. Catalytic hydrogenation is conveniently carried out in the temperature range of 0° C.–150° C., but preferably at ambient temperature at slightly above atmospheric pressure.

A compound of the formula (VB) is conveniently prepared by reacting together compounds of the formulae (VC) and (VD):

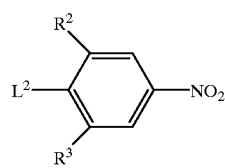

(VC)

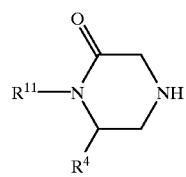

(VD)

wherein $R^2$–$R^4$ and $R^{11}$ are as hereinabove defined and $L^2$ is a leaving group, preferably halo and in particular fluoro.

The reaction between compounds of the formulae (VC) and (VD) is carried out in the presence of an organic or inorganic base such as sodium bicarbonate, potassium carbonate or an amine base such as diisopropylethylamine, in an inert solvent such as acetonitrile, DMF, DMPU or N-methylpyrrolidone, in a temperature range of 50° C.–150° C.

Compounds of the formula (VD) may be prepared by introducing $R^{11}$ into a compound of the formula (VE):

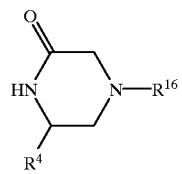

(VE)

wherein $R^{16}$ is a protecting group, and subsequently removing $R^{16}$ (deprotecting). Preferably $R^{16}$ is tert-butoxycarbonyl.

For example, when $R^{11}$ is a substituted or unsubstituted alkyl group, the compound of the formula (VE) may be reacted with $R^{11}$-$L^3$ wherein $L^3$ is a leaving group, in particular tosylate or halo in the presence of a strong base. Suitable bases include sodium hydroxide, lithium diisopropylamide, butyllithium and potassium butoxide. The reaction is usually performed in an inert solvent such as THF or DMF in a temperature range of 0° C.–100° C.

Alternatively, when $R^{11}$ is alkyl substituted by an electronegative group, $R^{11}$ may be introduced into the compound of the formula (VE) by reacting it with the related alkene. The compound of the formula (VD) wherein $R^{11}$ is 2-hydroxyethyl may be prepared by heating the compound of the formula (VE) with ethylene oxide in the temperature range of 40° C.–100° C.

It may be synthetically simpler to prepare some compounds of the formula (VD) by introducing a substituent onto the unsubstituted ring nitrogen in the compound of the formula (VE) which could subsequently be converted into the desired $R^{11}$. For example, 2-cyanoethyl could be introduced onto the ring nitrogen, and reduced to an amino group which itself could be alkylated to alkylamino.

The reaction of a compound of the formula (I) or (II) wherein $R^1$ or $R^{10}$ is hydroxy with an amide of the formula (VII) is conveniently carried out in the presence of tri-n-butylphosphine and 1,1'-(azodicarbonyl)dipiperidine in an organic solvent such as THF, and in the temperature range 0°–60° C., but preferably at ambient temperature. Details of analogous Mitsunobu reactions are contained in Tsunoda et al, Tet. Letts., 34, 1639, (1993). Amides of the formula (VII) may be prepared by standard procedures of organic chemistry which are within the ordinary skill of an organic chemist.

When an optically active form of a compound of the formula (I) is required, it may be obtained, by carrying out one of the above procedures using an optically active starting material or by resolution of a racemic form of the compound or intermediate using a standard procedure.

According to a further feature of the invention there is provided a compound of the formula (I), or a pharmaceutically-acceptable salt thereof, for use in a method of treatment of the human or animal body by therapy.

According to a further feature of the present invention there is provided a method for producing an antibacterial effect in a warm blooded animal, such as man, in need of such treatment, which comprises administering to said animal an effective amount of a compound of the present invention, or a pharmaceutically-acceptable salt thereof.

The invention also provides the use of a compound of the present invention, or a pharmaceutically-acceptable salt thereof, in the manufacture of a novel medicament for use in the production of an antibacterial effect in a warm blooded animal, such as man.

In order to use a compound of the formula (I) or a pharmaceutically-acceptable salt thereof for the therapeutic treatment of mammals including humans, in particular in treating infection, it is normally formulated in accordance with standard pharmaceutical practice as a pharmaceutical composition.

Therefore in another aspect of the present invention provides a pharmaceutical composition which comprises a compound of the formula (I) or a pharmaceutically-acceptable salt thereof and a pharmaceutically-acceptable carrier.

The pharmaceutical compositions of this invention may be administered in standard manner for the disease condition that it is desired to treat, for example by oral, rectal or parenteral administration. For these purposes the compounds of this invention may be formulated by means known in the art into the form of, for example, tablets, capsules, aqueous or oily solutions or suspensions, (lipid) emulsions, dispersible powders, suppositories, ointments, creams, eye drops, nasal drops and sterile injectable aqueous or oily solutions or suspensions.

In addition to the compounds of the present invention the pharmaceutical composition of this invention may also contain, or be co-administered with, one or more known drugs selected from other clinically useful antibacterial agents (for example β-lactams or aminoglycosides). These may include penicillins, for example oxacillin or flucloxacillin and carbapenems, for example meropenem or imipenem, to broaden the therapeutic effectiveness. Compounds of this invention may also contain or be co-administered with bactericidal/permeability-increasing protein (BPI) or efflux pump inhibitors to improve activity against Gram-negative bacteria and bacteria resistant to antimicrobial agents.

A suitable pharmaceutical composition of this invention is one suitable for oral administration in unit dosage form, for example a table or capsule which contains between 100 mg and 1 g of the compound of this invention.

In another aspect a pharmaceutical composition of the invention is one suitable for intravenous, subcutaneous or intramuscular injection.

Each patient may receive, for example, a daily intravenous, subcutaneous or intramuscular dose of 5 mgkg-$^1$ to 20 mgkg-$^1$ of the compound of this invention, the composition being administered 1 to 4 times per day. The intravenous, subcutaneous and intramuscular dose may be given by means of a bolus injection. Alternatively the intravenous dose may be given by continuous infusion over a period of time. Alternatively each patient will receive a daily oral dose which is approximately equivalent to the daily parenteral dose, the composition being administered 1 to 4 times per day.

Antibacterial Activity

The pharmaceutically-acceptable compounds of the present invention are useful antibacterial agents having a good spectrum of activity in vitro against standard Gram-positive organisms, which are used to screen for activity against pathogenic bacteria. Notably, the pharmaceutically-acceptable compounds of the present invention show activity against enterococci, pneumococci and methicillin resistant strains of *S. aureus* and coagulase negative staphylococci. The antibacterial spectrum and potency of a particular compound may be determined in a standard test system.

The antibacterial properties of the compounds of the invention may also be demonstrated in vivo in conventional tests. No overt toxicity or other untoward effects are observed when compounds of the formula I are so tested.

The following results were obtained on a standard in vitro test system. The activity is described in terms of the minimum inhibitory concentration (MIC) determined by the agar-dilution technique with an inoculum size of $10^4$ CFU/spot.

Staphylococci were tested on agar, using an inoculum of $10^4$ CFU/spot and an incubation temperature of 37° C. for 24 hours—standard test conditions for the expression of methicillin resistance.

Streptococci and enterococci were tested on agar supplemented with 5% defibrinated horse blood, an inoculum of $10^4$ CFU/spot and an incubation temperature of 37° C. in an atmosphere of 5% carbon dioxide for 48 hours—blood is required for the growth of some of the test organisms.

| Organism | MIC ($\mu$g/ml) Example 1 |
|---|---|
| *Staphylococcus aureus:* | |
| Oxford | 1 |
| Novb. Res | 2 |
| MRQS | 2 |
| MRQR | 4 |
| Coagulase Negative Staphylococci | |
| MS | 0.5 |
| MR | 1 |
| *Streptococcus pyogenes* C203 | 1 |
| *Enterococcus faecalis* | 2 |
| *Bacillus subtilis* | 1 |

Novb. Res = Novobiocin resistant
MRQS = methicillin resistant quinolone sensitive
MRQR = methicillin resistant quinolone resistant
MR = methicillin resistant The invention is now illustrated but not limited by the following Examples in which unless otherwise stated:

i) evaporations were carried out by rotary evaporation in vacuo and work-up procedures were carried out after removal of residual solids by filtration;

(ii) operations were carried out at ambient temperature, that is in the range of 18–26° C. and in air unless otherwise stated, or unless the skilled person would otherwise work under an inert atmosphere;

(iii) column chromatography (by the flash procedure) was performed on Merck Kieselgel silica (art. 9385);

(iv) yields are given for illustration only and are not necessarily the maximum attainable;

(v) the structures of the end-products of the formula I were confirmed by NMR and mass spectral techniques [proton magnetic resonance spectra were determined in D6-DMSO unless otherwise stated using a Varian Gemini 2000 spectrometer operating at a field strength of 300 MHz, or a Bruker AM250 spectrometer operating at a field strength of 250 MHz; chemical shifts are reported in parts per million downfield (δ scale), using tetramethylsilane as an internal standard when using CDCl$_3$ but otherwise using an internal signal when using D6-DMSO; and peak multiplicities are shown thus: s, singlet; d, doublet; dd, doublet of doublets; ddd, doublet of double doublets; t, triplet; q, quartet; dq, doublet of quartets; m, multiplet; dm, doublet of multiplets; br, broad; fast-atom bombardment (FAB) mass spectral data were obtained using a Platform spectrometer (supplied by Micromass) run in electrospray and, where appropriate, either positive ion data or negative ion data were collected];

(vi) intermediates were not generally fully characterised and purity was in general assessed by thin layer chromatographic, infra-red (IR), mass spectral (MS) or NMR analysis; and (vii) the following abbreviations have been used:

| | |
|---|---|
| DMF | N,N-dimethylformamide; |
| THF | tetrahydrofuran; |
| TFA | trifluoroacetic acid; |
| DMSO | dimethylsulfoxide; |
| CDCl$_3$ | deuterated chloroform; |
| CI | chemical ionization; |
| DMPU | 1,3-dimethyl-3,4,5,6-tetrahydro-2(1H)-pyrimidinone (N,N-dimethylpropylene urea). |

EXAMPLE 1

(5R)-5-Azidomethyl-3-(3-fluoro-4-{4-methyl-3-oxopiperazin-1-yl}phenyl)oxazolidin-2-one (820 mg) was dissolved in dry DMF (20 ml), and the solution purged with argon. Palladium (10% on carbon, 164 mg) was added, and the mixture stirred at ambient temperature for 2 hours under hydrogen confined in a balloon. Pyridine (0.38 ml) and acetic anhydride (0.44 ml) were added, and the mixture stirred at ambient temperature for 16 hours. The mixture was evaporated to dryness, and chromatographed on silica using as eluant a gradient increasing in polarity from 0 to 5% methanol in dichloromethane. Relevant fractions were combined and evaporated to give N-(5S)-[3-(3-fluoro-4-{4-methyl-3-oxopiperazin-1-yl}phenyl)-2-oxooxazolidin-5-ylmethyl]acetamide (350 mg).

MS (Electrospray): 365 (MH$^+$).

NMR (CDCl$_3$) δ: 2.02 (s,3H); 3.03 (s,3H); 3.42 (t,2H); 3.46 (t,2H); 3.55–3.72 (m, 2H); 3.76, 3.77 (s+dd, 2H+1H); 4.06 (t,1H); 4.76 (m,1H); 6.17 (br t, 1H); 6.91 (t, 1H); 7.08 (dm, 1H); 7.48 (dd,1H).

The (5R)-5-azidomethyl-3-(3-fluoro-4-{4-methyl-3-oxopiperazin-1-yl}phenyl)oxazolidin-2-one used as starting material was obtained as follows:

1-tert-Butoxycarbonyl-3-oxopiperazine (see Tetrahedron Lett. (1980), 21(32), 3019–20 for outline of synthesis, 5 g) was dissolved in dry DMF (75 ml) and potassium tert-butoxide (3.08 g) was added. The mixture was stirred at ambient temperature for 1 hour, then iodomethane (3.9 g) was added, and stirring continued at the same temperature for 2.5 hours. Solvent was evaporated, and the residue chromatographed on silica, using as eluant a gradient increasing in polarity from 0 to 100% ethyl acetate in iso-hexane. Relevant fractions were combined and evaporated to give 1-tert-butoxycarbonyl-4-methyl-3-oxopiperazine (3.92 g).

MS (CI): 215 (MH$^+$).

NMR (CDCl$_3$) δ: 1.48 (s,9H); 3.01 (s,3H); 3.35 (t,2H); 3.66 (t,2H); 4.08 (s, 2H).

1-tert-Butoxycabonyl-4-methyl-3-oxopiperazine (3.87 g) was dissolved in trifluoroacetic acid (80 ml), and the mixture stirred at ambient temperature for 2 hours. Solvent was evaporated to give 1-methyl-2-oxopiperazine as a trifluoroacetate salt, with some excess trifluoroacetic acid.

MS (CI): 114 (MH$^+$).

NMR (CDCl$_3$) δ: 3.11 (s,3H); 3.62 (t,2H); 3.72 (t,2H); 4.05 (s,2H).

N,N-Diisopropylethylamine (11.5 ml) and 1-methyl-2-oxopiperazine (4.12 g) were added to a solution of 3,4-difluoronitrobenzene (1.82 ml) in acetonitrile (100 ml), and the mixture heated to reflux for 16 hours. Solvent was evaporated, and the residue chromatographed on silica, using as eluant a gradient increasing in polarity from 0 to 100% ethyl acetate in iso-hexane. Relevant fractions were combined and evaporated to give 3-fluoro-4-(4-methyl-3-oxopiperazin-1-yl)nitrobenzene (3.37 g).

MS (CI): 254 (MH$^+$).

NMR (DMSO-D6) δ: 3.06 (s,3H); 3.53 (t,2H); 3.67 (t,2H); 3.97 (s,2H): 6.90 (t,1H); 7.95 (dd,1H); 8.02 (m,1H).

3-Fluoro-4-(4-methyl-3-oxopiperazin-1-yl)nitrobenzene (3.33 g) was dissolved in a mixture of DMF (40 ml) and methanol (10 ml), and the solution flushed with argon. Ammonium formate (4.15 g) was added, and the mixture cooled to 5° C. Palladium (10% on carbon, 104 mg) was added, and the temperature allowed to rise to ambient as the mixture was stirred under argon for 2 hours. Solvents were evaporated to give an air sensitive product, 5-amino-2-(4-methyl-3-oxopiperazin-1-yl)fluorobenzene, which was used as such in the next stage.

MS (CI): 224 (MH$^+$).

NMR (CDCl$_3$) δ: 3.02 (s,3H); 3.27 (t,2H); 3.42 (t,2H); 3.69 (s,2H); 4.13 (br s, 2H); 6.40 (m,1H); 6.44 (dd,1H); 6.77 (t,1H).

5-Amino-2-(4-methyl-3-oxopiperazin-1-yl)fluorobenzene (2.94 g) was dissolved in dry DMF (40 ml) under argon, and the solution cooled to −20° C. N,N-Dimethylaniline (2.1 ml) was added, followed by benzyl chloroformate (2.07 ml), and the mixture stirred for 10 minutes at −20° C. The temperature was allowed to rise to ambient over 16 hours. The mixture was diluted with ethyl acetate, and washed twice with water, and then brine. After drying (MgSO$_4$) and evaporation of solvent, the residue was chromatographed on silica, using as eluant a gradient increasing in polarity from 0 to 5% methanol in dichloromethane. Relevant fractions were combined and evaporated to give 5-benzyloxycarbonylamino-2-(4-methyl-3-oxopiperazin-1-yl)fluorobenzene (4.6 g).

MS (CI): 358 (MH$^+$).

NMR (CDCl$_3$) δ: 2.97 (s,3H); 3.31 (t,2H); 3.41 (t,2H); 3.70 (s,2H); 5.16 (s,2H); 6.81 (t,1H); 6.98 (m,2H); 7.33 (m,6H).

5-Benzyloxycarbonylamino-2-(4-methyl-3-oxopiperazin-1-yl)fluorobenzene (4.5 g) was dissolved in dry THF (100 ml) under argon and the solution cooled to −78° C. A solution of n-butyllithium (8.67 ml, 1.6 M in hexane) was added to this whilst keeping the temperature below −60° C. The mixture was stirred for 5 minutes and (R)-glycidylbutyrate (1.86 ml) was added. Stirring was continued at −78° C. for 30 minutes and the temperature then allowed to rise to ambient over 16 hours. The mixture was evaporated to dryness and then treated with dichloromethane. The mixture was filtered to give (5R)-3-(3-fluoro-4-{4-methyl-3-oxopiperazin-1-yl}phenyl)-5-hydroxymethyloxazolidin-2-one (409 mg). The residual organic solution was washed twice with water, and then brine. After drying (MgSO$_4$) and evaporation of solvent, the residue was chromatographed on silica, using as eluant a gradient increasing in polarity from 0 to 6% methanol in dichloromethane. Relevant fractions were combined and evaporated to give further (5R)-3-(3-fluoro-4-{4-methyl-3-oxopiperazin-1-yl}phenyl)-5-hydroxymethyloxazolidin-2-one product (535 mg).

MS (CI): 324 (MH$^+$).

NMR (CDCl$_3$+DMSO-D6) δ: 2.99 (s,3H); 3.38 (t,2H); 3.48 (t,2H); 3.67, 3.70 (m+s, 3H); 3.82 (m,1H); 3.94 (dd,

1H); 4.03 (t,1H); 4.69 (m,1H); 5.09 (t,1H); 6.95 (t,1H); 7.14 (dd,1H); 7.56 (dd,1H).

(5R)-3-(3-Fluoro-4-{4-methyl-3-oxopiperazin-1-yl}phenyl)-5-hydroxymethyloxazolidin-2-one (900 mg) was dissolved in pyridine (20 ml), and cooled to 0° C. Triethylamine (0.5 ml) and methanesulfonyl chloride (0.24 ml) were added, and stirring continued at 5° C. for 2 hours. Solvent was evaporated, and the residue chromatographed on silica, using as eluant a gradient increasing in polarity from 0 to 3% methanol in dichloromethane. Relevant fractions were combined and evaporated to give (5R)-3-(3-fluoro-4-{4-methyl-3-oxopiperazin-1-yl}phenyl)-5-(methanesulfonyloxymethyl)oxazolidin-2-one (990 mg).

MS (Electrospray): 402 (MH$^+$).

NMR (CDCl$_3$) δ: 3.04 (s,3H); 3.11 (s,3H); 3.42 (dt, 4H); 3.77 (s,2H); 3.93 (dd,1H); 4.13 (t,1H); 4.48 (dq,2H); 4.92 (m,1H); 6.92 (t,1H); 7.11 (dd,1H); 7.50 (dd,1H).

Sodium azide (924 mg) was added to a solution of (5R)-3-(3-fluoro-4-{4-methyl-3-oxopiperazin-1-yl}phenyl)-5-(methanesulfonyloxymethyl)oxazolidin-2-one (950 mg) in dry DMF (50 ml), and the mixture heated at 75° C. for 2 hours. The mixture was diluted with ethyl acetate and washed with three portions of water. The aqueous layer was then back-extracted with two portions of ethyl acetate, and the combined organic extracts dried over MgSO$_4$. Evaporation gave (5R)-5-azidomethyl-3-(3-fluoro-4-{4-methyl-3-oxopiperazin-1-yl}phenyl)oxazolidin-2-one product which was used without further purification.

MS (CI): 402 (MH$^+$).

NMR (CDCl$_3$) δ: 3.03 (s,3H); 3.42 (dm,4H); 3.59 (dd, 1H); 3.71 (dd,1H); 3.77 (s, 2H); 3.83 (dd,1H); 4.06 (t,1H); 4.80 (m,1H); 6.91 (t,1H); 7.12 (dm,1H); 7.51 (dd,1H).

EXAMPLE 2

(5R)-5-Azidomethyl-3-(3-fluoro-4-{4-ethyl-3-oxopiperazin-1-yl-}phenyl)oxazolidin-2-one (750 mg) was dissolved in a mixture of DMF (5 ml) and ethyl acetate (10 ml), and the solution purged with argon. Palladium (10% on carbon, 150 mg) was added, followed by acetic anhydride (0.4 ml) and the mixture stirred at ambient temperature under hydrogen confined in a balloon for 2 hours. The mixture was filtered through celite, evaporated to dryness, and chromatographed on silica, using as eluant a gradient increasing in polarity from 0 to 10% methanol in dichloromethane. Relevant fractions were combined and evaporated, and the residue purified by crystallisation from acetonitrile to give N-(5S)-[3-(3-fluoro-4-{4-ethyl-3-oxopiperazin-1-yl}phenyl)-2-oxooxazolidin-5-ylmethyl]acetamide (145 mg).

MS (Electrospray): 379 (MH$^+$).

NMR (DMSO-D6) δ: 1.06 (t,3H); 1.83 (s,3H); 3.25–3.45 (overlapping m,8H); 3.59 (s, 2H); 3.70 (dd,1H); 4.17 (t,1H); 4.70 (m,1H); 7.17 (t,1H); 7.35 (dd,1H); 7.51 (dd, 1H); 8.19 (br t,1H).

The (5R)-5-azidomethyl-3-(3-fluoro-4-{4-ethyl-3-oxopiperazin-1-yl}phenyl)oxazolidin-2-one used as starting material was prepared as follows:

1-tert-Butoxycarbonyl-3-oxopiperazine (7.5 g) was dissolved in dry DMF (250 ml) and potassium tert-butoxide (8.4 g) was added. The mixture was stirred at ambient temperature for 30 minutes, then iodoethane (3.3 ml) added, and stirring continued at the same temperature for 24 hours. A further equal portion of iodoethane was added and stirring continued for 24 hours. Solvent was evaporated, and the residue partitioned between ethyl acetate and water. The organic layer was washed with water, evaporated, and purified by chromatography on silica, using as eluant a gradient increasing in polarity from 0 to 25% isopropanol in iso-hexane. Relevant fractions were combined and evaporated to give 1-tert-butoxycarbonyl-4-ethyl-3-oxopiperazine (6.0 g).

MS (CI): 229 (MH$^+$).

NMR (CDCl$_3$) δ: 1.16 (t,3H); 1.47 (s,9H); 3.34 (t,2H); 3.46 (q,2H); 3.64 (t,2H); 4.06 (s,2H).

1-tert-Butoxycarbonyl-4-ethyl-3-oxopiperazine (5.9 g) was dissolved in dichloromethane (100 ml), cooled in an ice-bath, and trifluoroacetic acid (145 ml) added. The mixture was stirred at the same temperature for 2 hours. Solvent was evaporated to yield 1-ethyl-2-oxopiperazine product as a salt with 3 moles of trifluoroacetic acid.

MS (CI): 129 (MH$^+$).

NMR (DMSO-D6+CD$_3$CO$_2$H) δ: 1.09 (t,3H); 3.41, 3.45 (q+t,4H); 3.54 (t,2H); 3.76 (s,2H).

1-Ethyl-2-oxopiperazine (3TFA salt, 10.5 g) was dissolved in acetonitrile (200 ml), and N,N-diisopropylethylamine (19.5 ml) followed by 3,4-difluoronitrobenzene (2.25 ml) were added. The mixture was heated to reflux for 18 hours. Solvent was evaporated, and the residue chromatographed on silica using as eluant a gradient increasing in polarity from 0 to 4% methanol in dichloromethane. Relevant fractions were combined and evaporated to give a solid containing some N,N-diisopropylethylamine trifluoroacetate. The solid was purified by dissolving in ethyl acetate and washing well with water. Evaporation of the organic layer gave 3-fluoro-4-(4-ethyl-3-oxopiperazin-1-yl)nitrobenzene as a solid (3.44 g).

MS (CI): 268 (MH$^+$).

NMR (CDCl$_3$) δ: 1.21 (t,3H); 3.50, 3.52 (q+t,4H); 3.64 (t,2H); 3.96 (s,2H); 6.88 (t, 1H); 7.95 (dd,1H); 8.02 (dd,1H).

3-Fluoro-4-(4-ethyl-3-oxopiperazin-1-yl)nitrobenzene (3.4 g) was dissolved in ethyl acetate (200 ml) and the solution flushed with argon. Palladium (10% on carbon, 180 mg) was added, and the mixture hydrogenated under ambient pressure. After gas uptake had ceased, the mixture was filtered through celite and solvent evaporated to give 5-amino-2-(4-ethyl-3-oxopiperazin-1-yl)fluorobenzene, which was used without further purification.

MS (Electrospray): 238 (MH$^+$).

NMR (CDCl$_3$) δ: 1.17 (t,3H); 3.25 (t,2H); 3.41 (t,2H); 3.48 (q,2H); 3.61 (br s,2H); 3.66 (s,2H); 6.38 (dd,1H); 6.42 (dd,1H); 6.77 (t,1H).

5-Amino-2-(4-ethyl-3-oxopiperazin-1-yl)fluorobenzene (2.95 g) was dissolved in dry dichloromethane (50 ml) under argon. Pyridine (1.26 ml) was added, and the mixture cooled to −20° C. Benzyl chloroformate (1.95 ml) was added, and the mixture stirred for 10 minutes at −20° C., before allowing the temperature to rise to ambient over 1.5 hours. Solvents were evaporated, the residue dissolved in dichloromethane and washed with sodium bicarbonate solution. After drying (MgSO$_4$) and evaporation of solvent, the residue was chromatographed on silica, using as eluant a gradient increasing in polarity from 0 to 4% methanol in dichloromethane. Relevant fractions were combined and evaporated to give 5-benzyloxycarbonylamino-2-(4-ethyl-3-oxopiperazin-1-yl)fluorobenzene (3.3 g).

MS (Electrospray): 372 (MH$^+$).

NMR (CDCl$_3$) δ: 1.18 (t,3H); 3.33 (t,2H); 3.45 (t,2H); 3.50 (q,2H); 3.72 (s,2H); 5.20 (s,2H); 6.76 (br s,1H); 6.82 (t,1H); 6.96 (dd,1H); 7.40 (m,6H).

5-Benzyloxycarbonylamino-2-(4-ethyl-3-oxopiperazin-1-yl)fluorobenzene (3.25 g) was dissolved in dry THF (100 ml) under argon. The solution was cooled to −78° C., and treated with a solution of n-butyllithium (1.6 M in hexane, 6.02 ml), keeping the temperature below −60° C. 1,3-Dimethyl-3,4,5,6-tetrahydro-2(1H)-pyrimidone (DMPU, 10 ml) was added to the resulting mixture to facilitate stirring, and (R)-glycidylbutyrate (1.29 ml) added. Stirring was continued at −78° C. for 30 minutes, before allowing the temperature to rise to ambient over 16 hours. Sodium bicarbonate solution (50 ml) was added, followed by sufficient ethyl acetate to form two layers. The organic layer was separated, washed twice with water, dried (MgSO$_4$) and evaporated. The residue was chromatographed on silica, using as eluant a gradient increasing in polarity from 0 to 6% methanol in dichloromethane. Relevant fractions were combined and evaporated to give (5R)-3-(3-fluoro-4-{4-ethyl-3-oxopiperazine-1-yl}phenyl)-5-hydroxymethyloxazolidin-2-one (990 mg).

MS (Electrospray): 338 (MH$^+$).

NMR (DMSO-D6) δ: 1.08 (t,3H); 3.28–3.41 (overlapping m,6H); 3.59 (s+ddd,3H); 3.66 (ddd,1H); 3.80 (dd,1H); 4.05 (t,1H); 4.67 (m,1H); 5.16 (t,1H); 7.05 (t,1H); 7.22 (dd,1H); 7.55 (dd,1H).

(5R)-3-(3-Fluoro-4-{4-ethyl-3-oxopiperazin-1-yl}phenyl)-5-hydroxymethyloxazolidin-2-one (830 mg) was dissolved in pyridine (20 ml), and cooled to 0° C. Triethylamine (0.41 ml) and methanesulfonyl chloride (0.21 ml) were added, and stirring continued at ambient temperature for 2 hours. Solvent was evaporated and the residue dissolved in ethyl acetate. The resulting solution was washed with water, dried (MgSO$_4$), and evaporated to give (5R)-3-(3-fluoro-4-{4-ethyl-3-oxopiperazin-1-yl}phenyl)-5-(methanesulfonyloxymethyl)-oxazolidin-2-one (1.0 g) which was used without further purification.

MS (Electrospray): 416 (MH$^+$).

NMR (CDCl$_3$) δ: 1.20 (t 3H); 3.11 (s,3H); 3.30–3.55 (m,6H); 3.78 (s,2H); 3.94 (dd, 1H); 4.14 (t,1H); 4.46 (dq, 2H); 4.93 (m,1H); 6.92 (t,1H); 7.11 (dd,1H); 7.49 (dd, 1H).

(5R)-3-(3-Fluoro-4-{4-ethyl-3-oxopiperazin-1-yl}phenyl)-5-(methanesulfonyloxymethyl)-oxazolidin-2-one (950 mg) was dissolved in dry DMF (30 ml) and sodium azide (893 mg) was added. The mixture was heated at 80° C. for 5 hours, and then evaporated to dryness. The residue was dissolved in ethyl acetate and the resulting solution washed with water and dried (MgSO$_4$). The crude product so obtained was chromatographed on silica, using as eluant a gradient increasing in polarity from 0 to 6% methanol in dichloromethane. Relevant fractions were combined and evaporated to give (5R)-5-azidomethyl-3-(3-fluoro-4-{4-ethyl-3-oxopiperazin-1-yl}phenyl)oxazolidin-2-one (777 mg).

MS (Electrospray): 363 (MH$^+$).

NMR (CDCl$_3$) δ: 1.20 (t,3H); 3.38 (m,2H); 3.45 (m,2H); 3.50 (q,2H); 3.58 (dd,1H); 3.71 (dd,1H); 3.78 (s,2H); 3.83 (dd,1H); 4.06 (t,1H); 4.79 (m,1H); 6.91 (t,1H); 7.11 (dm, 1H); 7.52 (dd,1H).

EXAMPLE 3

(5R)-5-Azidomethyl-3-(3-fluoro-4-{4-(2-methoxyethyl)-3-oxopiperazin-1-yl}phenyl)oxazolidin-2-one (750 mg) was dissolved in ethyl acetate (15 ml), and the solution purged with argon. Palladium (10% on carbon, 150 mg) was added, followed by acetic anhydride (0.36 ml) and the mixture stirred at ambient temperature under hydrogen confined in a balloon for 2 hours. The mixture was filtered through celite, evaporated to dryness, and chromatographed on silica, using as eluant a gradient increasing in polarity from 0 to 5% methanol in dichloromethane. Relevant fractions were combined and evaporated, to give N-(5S)-[3-(3-fluoro-4-{4-(2-methoxyethyl)-3-oxopiperazin-1-yl}phenyl)-2-oxooxazolidin-5-ylmethyl]acetamide (228 mg).

MS (Electrospray): 409 (MH$^+$).

NMR (CDCl$_3$) δ: 2.03 (s,3H); 3.35 (s+t,5H); 3.63 (s+overlapping m,8H); 3.77 (s+overlapping m,3H); 4.03 (t,1H); 4.77 (m,1H); 6.14 (br t,1H); 6.90 (t,1H); 7.08 (dm, 1H); 7.47 (dd,1H).

The (5R)-5-azidomethyl-3-(3-fluoro-4-{4-(2-methoxyethyl)-3-oxopiperazin-1-yl}phenyl)oxazolidin-2-one used as starting material was prepared as follows:

1-tert-Butoxycarbonyl-3-oxopiperazine (7.5 g) was dissolved in dry DMF (250 ml) and potassium tert-butoxide (8.4 g) was added. The mixture was stirred at ambient temperature for 30 minutes, then 1-bromo-2-methoxyethane (3.9 ml) added, and stirring continued at the same temperature for 24 hours. A further equal portion of 1-bromo-2-methoxyethane was added and stirring continued for 24 hours. Solvent was evaporated, and the residue partitioned between ethyl acetate and water. The organic layer was washed with water and evaporated to give the1-tert-butoxycarbonyl-4-(2-methoxyethyl)-3-oxopiperazine (6.7 g) which was used without further purification.

MS (Electrospray): 259 (MH$^+$).

NMR (CDCl$_3$) δ: 1.45 (s,9H); 3.36 (s,3H); 3.48 (t,2H); 3.65 (m,4H); 3.65 (t,2H); 4.10 (s,2H).

1-tert-Butoxycarbonyl-4-(2-methoxyethyl)-3-oxopiperazine (6.6 g) was dissolved in dichloromethane (100 ml), the resulting solution cooled in an ice-bath, and trifluoroacetic acid (145 ml) added. The mixture was stirred at the same temperature for 2 hours. Solvent was evaporated to yield 1-(2-methoxyethyl)-2-oxopiperazine product as a salt with 4 moles of trifluoroacetic acid.

MS (CI): 159 (MH$^+$).

NMR (DMSO-D6+CD$_3$CO$_2$H) δ: 3.30 (s,3H); 3.43 (t,2H); 3.54 (m,4H); 3.64 (t,2H); 3.78 (s,2H).

1-(2-Methoxyethyl)-2-oxopiperazine (4TFA salt, 13.5 g) was dissolved in acetonitrile (200 ml), and N,N-diisopropylethylamine (22.6 ml) followed by 3,4-difluoronitrobenzene (2.2 ml) were added. The mixture was heated to reflux for 18 hours. Solvent was evaporated, and the residue chromatographed on silica, using as eluant a gradient increasing in polarity from 0 to 4% methanol in dichloromethane. Relevant fractions were combined and evaporated to give a solid containing some N,N-diisopropylethylamine trifluoroacetate. The solid was purified by dissolving in ethyl acetate and washing well with water. Evaporation of the organic layer gave 3-fluoro-4-(4-{2-methoxyethyl}-3-oxopiperazin-1-yl)nitrobenzene as a solid (4.07 g).

MS (CI): 298 (MH$^+$).

NMR (CDCl$_3$) δ: 3.31 (s,3H); 3.63 (m,6H); 4.00 (s,2H); 6.89 (t,1H); 7.95 (dd,1H); 8.02 (dm,1H).

3-Fluoro-4-(4-{2-methoxyethyl}-3-oxopiperazin-1-yl) nitrobenzene (4 g) was dissolved in a mixture of ethyl acetate (200 ml) and DMF (5 ml), and the solution flushed with argon. Palladium (10% on carbon, 200 mg) was added, and the mixture hydrogenated under ambient pressure. After gas uptake had ceased, the mixture was filtered through celite and solvent was evaporated to give 5-amino-2-(4-{2-methoxyethyl}-3-oxopiperazin-1-yl)fluorobenzene which was used without further purification.

MS (Electrospray): 268 (MH$^+$).

NMR (CDCl$_3$) δ: 3.25 (t,2H); 3.36 (s,3H); 3.55 (t,2H); 3.61 (s,4H); 3.64 (br s,2H); 3.70 (s,2H); 6.40 (dd,1H); 6.44 (dd,1H); 6.77 (t,1H).

5-Amino-2-(4-{2-methoxyethyl}-3-oxopiperazin-1-yl) fluorobenzene (3.5 g) was dissolved in dry dichloromethane (50 ml) under argon. Pyridine (1.33 ml) was added, and the mixture cooled to −20° C. Benzyl chloroformate (2.06 ml) was added, and the mixture stirred for 10 minutes at −20° C., before allowing the temperature to rise to ambient over 1.5 hours. Solvents were evaporated, the residue dissolved in dichloromethane and washed with sodium bicarbonate solution. After drying (MgSO$_4$) and evaporation of solvent, the residue was chromatographed on silica, using as eluant a gradient increasing in polarity from 0 to 4% methanol in dichloromethane. Relevant fractions were combined and evaporated to give 5-benzyloxycarbonylamino-2-(4-{2-methoxyethyl}-3-oxopiperazin-1-yl)fluorobenzene (3.28 g).

MS (Electrospray): 402 (MH$^+$).

NMR (CDCl$_3$) δ: 3.32 (t,2H); 3.34 (s,3H); 3.56 (t,2H); 3.62 (s,4H); 3.75 (s,2H); 5.19 (s,2H); 6.82 (t,1H); 6.84 (s,1H); 6.97 (dd,1H); 7.35 (m,6H).

5-Benzyloxycarbonylamino-2-(4-{2-methoxyethyl}-3-oxopiperazin-1-yl)fluorobenzene (3.2 g) was dissolved in dry THF (100 ml) under argon, cooled to −78° C., and treated with a solution of n-butyllithium (1.6 M in hexane, 5.5 ml), keeping the temperature below −60° C. 1,3-Dimethyl-3,4,5,6-tetrahydro-2(1H)-pyrimidone (DMPU, 10 ml) was added to the resulting mixture to facilitate stirring and (R)-glycidylbutyrate (0.93 ml) was added. The mixture was stirred at −78° C. for 30 minutes, before allowing the temperature to rise to ambient over 16 hours. Sodium bicarbonate solution (50 ml) was added, and the whole evaporated to dryness. Organic materials were dissolved from the residue using dichloromethane, and purified by chromatography on silica using as eluant a gradient increasing in polarity from 0 to 10% methanol in dichloromethane. Relevant fractions were combined and evaporated to give (5R)-3-(3-fluoro-4-{4-(2-methoxyethyl)-3-oxopiperazin-1-yl}phenyl)-5-hydroxymethyloxazolidin-2-one (1.14 g).

MS (Electrospray): 368 (MH$^+$).

NMR (DMSO-D6) δ: 3.27 (s+m,5H); 3.50 (t,2H); 3.53 (m,4H); 3.60 (m,1H); 3.66 (s, 2H); 3.71 (m,1H); 3.83 (dd,1H); 4.08 (t,1H); 4.71 (m,1H); 5.20 (t,1H); 7.09 (t,1H); 7.24 (dd,1H); 7.57 (dd,1H).

(5R)-3-(3-Fluoro-4-{4-(2-methoxyethyl)-3-oxopiperazin-1-yl}phenyl)-5-hydroxymethyloxazolidin-2-one (1.0 g) was dissolved in pyridine (25 ml), and cooled to 0° C. Triethylamine (0.46 ml) and methanesulfonyl chloride (0.23 ml) were added, and stirring continued at ambient temperature for 2 hours. Solvent was evaporated and the residue dissolved in ethyl acetate, washed with water, dried (MgSO$_4$), and evaporated to give (5R)-3-(3-fluoro-4-{4-(2-methoxyethyl)-3-oxopiperazin-1-yl}phenyl)-5-(methanesulfonyloxymethyl)oxazolidin-2-one (1.01 g) which was used without further purification.

MS (Electrospray): 446 (MH$^+$).

NMR (CDCl$_3$) δ: 3.11 (s, 3H); 3.36 (s, 3H); 3.37 (t, 2H); 3.58 (t, 2H); 3.63 (m, 4H); 3.80 (s, 2H); 3.93 (dd, 1H); 4.13 (t, 1H); 4.43 (dd, 1H); 4.50 (dd, 1H); 4.92 (m, 1H); 6.92 (t, 1H); 7.11 (dm, 1H); 7.48 (dd, 1H).

(5R)-3-(3-Fluoro-4-{4-(2-methoxyethyl)-3-oxopiperazin-1-yl}phenyl)-5-(methanesulfonyl-oxymethyl) oxazolidin-2-one (990 mg) was dissolved in dry DMF (30 ml), sodium azide (868 mg) was added, and the mixture heated at 80° C. for 4 hours. The mixture was evaporated to dryness, and the residue dissolved in ethyl acetate and washed with three portions of water. The aqueous layer was back-extracted with two portions of ethyl acetate, and the combined organic extracts dried over MgSO$_4$. Evaporation gave (5R)-5-azidomethyl-3-(3-fluoro-4-{4-(2-methoxyethyl)-3-oxopiperazin-1-yl}phenyl)oxazolidin-2-one (770 mg) which was used without further purification.

MS (Electrospray): 393 (MH$^+$)

NMR (CDCl$_3$) δ: 3.36 (s, 3H); 3.37 (t, 2H); 3.62 (overlapping m, 7H); 3.71 (dd, 1H); 3.78 (s, 2H); 3.83 (dd, 1H); 4.06 (t, 1H); 4.78 (m, 1H); 6.91 (t, 1H); 7.12 (dm, 1H); 7.49 (dd, 1H).

EXAMPLE 4

(5R)-5-Azidomethyl-3-(3-fluoro-4-{4-(2-fluoroethyl)-3-oxopiperazin-1-yl}phenyl)oxazolidin-2-one (360 mg) was dissolved in dry DMF (20 ml), and the solution purged with argon. Palladium (10% on carbon, 72 mg) was added, followed by acetic anhydride (0.17 ml) and the mixture stirred at ambient temperature under hydrogen confined in a balloon for 3 hours. The mixture was filtered through celite, evaporated to dryness, and partitioned between ethyl acetate and water. The organic extract was washed with brine, dried (MgSO$_4$), and evaporated. The residue was chromatographed on silica, using as eluant a gradient increasing in polarity from 0 to 2.5% methanol in dichloromethane. Relevant fractions were combined and evaporated, to give N-(5S)-[3-(3-fluoro-4-{4-(2-fluoroethyl)-3-oxopiperazin-1-yl}phenyl)-2-oxooxazolidin-5-ylmethyl]acetamide (166 mg).

MS (Electrospray): 397 (MH$^+$)

NMR (CDCl$_3$) δ: 2.02 (s, 3H); 3.38 (t, 2H); 3.61 (t+overlapping m, 3H); 3.70 overlapping m, 3H); 3.81 (s+overlapping m, 3H); 4.03 (t, 1H); 4.58 (t, 1H); 4.75 (t, 1H); 4.80 (m, 1H); 6.19 (br t, 1H); 6.91 (t, 1H); 7.09 (dm, 1H); 7.51 (dd, 1H).

The (5R)-5-azidomethyl-3-(3-fluoro-4-{4-(2-fluoroethyl)-3-oxopiperazin-1-yl}phenyl)oxazolidin-2-one used as starting material was prepared as follows:

1-tert-Butoxycarbonyl-3-oxopiperazine (21.6 g) was dissolved in dry DMF (500 ml) and poptassium tert-butoxide (24.2 g) was added. The mixture was stirred at ambient temperature for 30 minutes, then 1-(4-methylphenylsulfonyloxy)-2-fluoroethane (see J. Med. Chem. (1980), 23(9), 985–90 for outline of synthesis, 25.9 g) added, and stirring continued at the same temperature for 24 hours. Solvent was evaporated, and the residue partitioned between ethyl acetate and water. The organic layer was washed with water and evaporated. The residue was dissolved in isopropanol and diluted with iso-hexane, precipitating unchanged piperazinone starting material, which was removed by filtration. The solution was chromatographed on silica, using as eluant a gradient increasing in polarity from 0 to 50% isopropanol in iso-hexane. Relevant fractions were combined and evaporated to give 1-tert-butoxycarbonyl-4-(2-fluoroethyl)-3-oxopiperazine (6.74 g).

MS (CI): 247 (MH$^+$)

NMR (CDCl$_3$) δ: 1.49 (s, 9H); 3.50 (t, 2H); 3.66 (overlapping m, 3H); 3.77 (t, 1H); 4.11 (s, 2H); 4.53 (t, 1H); 4.72 (t, 1H).

1-t-Butoxycarbonyl-4-(2-fluoroethyl)-3-oxopiperazine (6.65 g) was dissolved in dichloromethane (500 ml), cooled in an ice-bath, and trifluoroacetic acid (150 ml) added. The mixture was stirred at the same temperature for 2 hours. Solvent was evaporated to yield crude product, which was dissolved in the minimum volume of ethyl acetate. Slow addition of diethyl ether caused precipitation of 1-(2-fluoroethyl)-2-oxopiperazine product as the mono trifluoroacetic acid salt (6.19 g).

MS (CI): 147 (MH$^+$)

NMR (DMSO-D6+CD$_3$CO$_2$H) δ: 3.44 (t, 2H); 3.63 (t overlapping m, 3H); 3.76 (t, 1H); 3.81 (s, 2H); 4.50 (t, 1H); 4.69 (t, 1H).

1-(2-Fluoroethyl)-2-oxopiperazine trifluoroacetate (6.1 g) was dissolved in acetonitrile (100 ml). N,N-Diisopropylethylamine (13 ml) was added to the mixture, followed by 3,4-difluoronitrobenzene (3.39 g), and the mixture heated to reflux for 18 hours. Solvent was evaporated, and the residue chromatographed on silica, using as eluant a gradient increasing in polarity from 0 to 4% methanol in dichloromethane. Relevant fractions were combined and evaporated to give 3-fluoro-4-(4-{2-fluoroethyl}-3-oxopiperazin-1-yl)nitrobenzene product as a solid (4.4 g).

MS (Electrospray): 286 (MH$^+$)

NMR (CDCl$_3$) δ: 3.67 (s, 4H); 3.72 (t, 1H); 3.83 (t, 1H); 4.02 (s, 2H); 4.58 (t, 1H); 4.76 (t, 1H); 6.91 (t, 1H); 7.96 (dd, 1H); 8.02 (dm, 1H).

3-Fluoro-4-(4-{2-fluoroethyl}-3-oxopiperazin-1-yl) nitrobenzene (4.35 g) was dissolved in a mixture of ethyl acetate (250 ml) and DMF (5 ml), and the solution flushed with argon. Palladium (10% on carbon, 200 mg) was added, and the mixture hydrogenated under ambient pressure. After gas uptake had ceased, the mixture was filtered through celite and solvent evaporated. The residue was taken up in ethyl acetate, washed twice with water, dried (MgSO$_4$), and evaporated, to give 5-amino-2-(4-}2-fluoroethyl}-3-oxopiperazin-1-yl)fluorobenzene product, which was used without further purification.

MS (Electrospray): 256 (MH$^+$)

NMR (CDCl$_3$) δ: 3.28 (t, 2H); 3.58 (t, 2H); 3.61 (br s, 2H); 3.68 (t, 1H); 3.72 (s, 2H); 3.80 (t, 1H); 4.56 (t, 1H); 4.75 (t, 1H); 6.40 (dd, 1H); 6.44 (dd, 1H); 6.78 (t, 1H). 5-Amino-2-(4-{2-fluoroethyl}-3-oxopiperazin-1-yl) fluorobenzene (2.6 g) was dissolved in dry dichloromethane (50 ml) under argon. Pyridine (1.03 ml) was added, and the mixture cooled to −20° C. Benzyl chloroformate (1.6 ml) was added, and the mixture stirred for 10 minutes at −20° C., before allowing the temperature to rise to ambient over 1.5 hours. Solvents were evaporated, the residue dissolved in dichloromethane and washed with sodium bicarbonate solution. After drying (MgSO$_4$) and evaporation of solvent, the residue was chromatographed on silica, using as eluant a gradient increasing in polarity from 0 to 5% methanol in dichloromethane. Relevant fractions were combined and evaporated to give 5-benzyloxycarbonylamino-2-(4-{2-fluoroethyl}-3-oxopiperazin-1-yl)fluorobenzene (3.43 g).

MS (Electrospray): 390 (MH$^+$)

NMR (CDCl$_3$) δ: 3.35 (t, 2H); 3.58 (t, 2H); 3.67 (t, 1H); 3.76 (s, 2H); (s, 2H); 3.78 (t, 1H); 4.55 (t, 1H); 4.75 (t, 1H); 5.20 (s, 2H); 6.71 (br s, 1H); 6.85 (t, 1H); 6.99 (dd, 1H); 7.37 (m, 6H).

A solution of lithium tert-butoxide was prepared by addition of n-butyllithium (1.6 m in hexane, 2.9 ml) to a stirred solution of tert-butanol (0.43 g) in anhydrous THF (10 ml) at −10° C. under argon. After cooling to −70° C., a solution of 5-benzyloxycarbonylamino-2-(4-{2-fluoroethyl}-3-oxopiperazin-1-yl)fluorobenzene (1.5 g) in dry THF (15 ml) was added. After 10 minutes, (R)-glycidylbutyrate (0.67 g) in dry THF (15 ml) was added to the resulting mixture, and stirring continued at −70° C. for 15 minutes, before allowing the temperature to rise to ambient over 16 hours. Methanol (10 ml) was added, followed by saturated sodium bicarbonate solution (20 ml) and water (10 ml). The organics were extracted into ethyl acetate (3×25 ml), washed with brine and dried (MgSO$_4$). Solvent was evaporated and the residue purified by chromatography on silica, using as eluant a gradient increasing in polarity from 0 to 3% methanol in dichloromethane. Relevant fractions were combined and evaporated to give (5R)-3-(3-fluoro-4-{4-(2-fluoroethyl)-3-oxopiperazin-1-yl}phenyl)-5-hydroxymethyloxazolidin-2-one (1.07 g).

MS (Electrospray): 356 (MH$^+$)

NMR (DMSO-D6) δ:3.32 (t, 2H); 3.50 (t, 2H); 3.66, 3.55–3.70 (s overlapping m, 5H); 3.63 (t, 1H); 3.78 (dd, 1H); 4.05 (t, 1H); 4.49 (t, 1H); 4.68 (t+m, 2H); 5.17 (t, 1H); 7.07 (t, 1H); 7.22 (dd, 1H); 7.55 (dd, 1H).

(5R)-3-(3-Fluoro-4-{4-(2-fluoroethyl)-3-oxopiperazin-1-yl}phenyl)-5-hydroxymethyl-oxazolidin-2-one (0.8 g) was dissolved in pyridine (15 ml), and the mixture cooled to 0° C. Triethylamine (0.38 ml) and methanesulfonyl chloride (0.19 ml) were added to the mixture, and stirring continued at ambient temperature for 2 hours. Solvent was evaporated and the residue dissolved in dichloromethane, washed with water, brine, dried (MgSO$_4$), and evaporated. The resulting residue was titurated with diethyl ether to give (5R)-3-(3-fluoro-4-{4-(2-fluoroethyl)-3-oxopiperazine-1-yl}phenyl)-5-(methanesulfonyloxymethyl)-oxazolidin-2-one (0.76 g) which was used without further purification.

MS (Electrospray): 432 (MH$^+$)

NMR (CDCl$_3$) δ: 3.12 (s, 3H); 3.41 (t, 2H); 3.62 (t, 2H); 3.71 (t, 1H); 3.79 (t, 1H); 3.81 (s, 2H); 3.94 (dd, 1H); 4.15 (t, 1H); 4.43 (dd, 1H); 4.51 (dd, 1H); 4.59 (t, 1H); 4.75 (t, 1H); 4.95 (m, 1H); 6.93 (t, 1H); 7.11 (dm, 1H); 7.50 (dd, 1H).

(5R)-3-(3-Fluoro-4-{4-(2-fluoroethyl)-3-oxopiperazin-1-yl}phenyl)-5-(methanesulfonyl-oxymethyl)oxazolidin-2-one (719 mg) was dissolved in dry DMF (15 ml), and sodium azide (647 mg) added to the mixture. The mixture was heated at 80° C. for 6 hours, and then evaporated to dryness. The resulting residue was dissolved in ethyl acetate, washed twice with water, and dried (MgSO$_4$). Evaporation gave (5R)-5-azidomethyl-3-(3-fluoro-4-(4-(2-fluoroethyl)-3-oxopiperazin-1-yl)phenyl)oxazolidin-2-one (413 mg) which was used without further purification.

MS (Electrospray): 381 (MH$^+$)

NMR (CDCl$_3$) δ: 3.39 (t, 2H); 3.61 (t overlapping m, 3H); 3.75 (m, 2H); 3.80 (s overlapping m, 3H); 3.83 (dd, 1H); 4.06 (t, 1H); 4.58 (t, 1H); 4.74 (t, 1H); 4.79 (m, 1H); 6.92 (t, 1H); 7.13 (dm, 1H); 7.51 (dd, 1H).

EXAMPLE 5

The following illustrate representative pharmaceutical dosage forms containing the compound of formula I, or a pharmaceutically-acceptable salt thereof (hereafter compound X), for therapeutic or prophylactic use in humans:

| (a) Tablet I | mg/tablet |
|---|---|
| Compound X | 100 |
| Lactose Ph.Eur | 179 |
| Croscarmellose sodium | 12 |

-continued

| | |
|---|---|
| Polyvinylpyrrolidone | 6 |
| Magnesium stearate | 3 |

| (b) Tablet II | mg/tablet |
|---|---|
| Compound X | 50 |
| Lactose Ph.Eur | 229 |
| Croscarmellose sodium | 12 |
| Polyvinylpyrrolidone | 6 |
| Magnesium stearate | 3 |

| (c) Tablet III | mg/tablet |
|---|---|
| Compound X | 1 |
| Lactose Ph.Eur | 92 |
| Croscarmellose sodium | 4 |
| Polyvinylpyrrolidone | 2 |
| Magnesium stearate | 1 |

| (d) Capsule | mg/capsule |
|---|---|
| Compound X | 10 |
| Lactose Ph.Eur | 389 |
| Croscarmellose sodium | 100 |
| Magnesium stearate | 1 |

| (e) Injection I | (50 mg/ml) |
|---|---|
| Compound X | 5.0% w/v |
| Isotonic aqueous solution | to 100% |

Buffers, pharmaceutically-acceptable cosolvents such as polyethylene glycol, polypropylene glycol, glycerol or ethanol or complexing agents such as hydroxy-jpropyl β cyclodextrin may be used to aid formulation.

Note

The above formulations may be obtained by conventional procedures well known in the pharmaceutical art. The tablets (a)–(c) may be enteric coated by conventional means, for example to provide a coating of cellulose acetate phthalate.

I claim:

1. A compound of the formula (I):

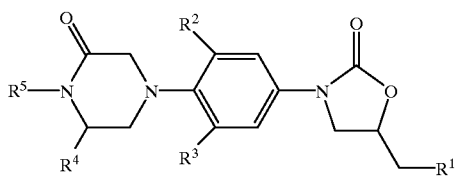

(I)

wherein:

$R^1$ is of the formula —NHC(=O)(1–4C)alkyl, —NHS(O)$_n$(1–4C)alkyl wherein n is 0, 1 or 2 or $R^1$ is hydroxy;

$R^2$ and $R^3$ are independently hydrogen or fluoro;

$R^4$ is hydrogen, methyl, ethyl or oxo;

$R^5$ is hydrogen, (1–6C)alkyl, (2–6C)alkenyl, (2–6C)alkynyl or of the formula $R^6(CH_2)_m$— wherein either: m is 1–4 and $R^6$ is trifluoromethyl, difluoromethyl, fluoromethyl, (1–4C)alkoxy, (1–4C)alkyl S(O)$_p$— wherein p is 0, 1 or 2, (1–6C)alkanoyloxy, di-(N-(1–4C)alkyl)amino, N-((1–4C)alkyl)(1–4C)alkanoylamino, cyano, carboxy, (1–4C)alkoxycarbonyl, carbamoyl, N-(1–4C)alkylcarbamoyl, di-(N-(1–4C)alkyl)carbamoyl, N-((1–4C)alkyl)(1–4C)alkanesulphonamido, $N^1$-((1–4C)alkyl)ureido, $N^1$-((1–4C)alkyl)-$N^3$-((1–4C)alkyl)ureido, $N^1$-((1–4C)alkyl)-di-(N$^3$-(1–4C)alkyl) ureido, or of the formula —OC(=O)NR$^7$(R$^8$) wherein R$^7$ and R$^8$ are independently hydrogen or (1–4C)alkyl or of the formula —N(R$^9$)SO$_2$NR$^7$(R$^8$) wherein R$^7$ and R$^8$ are as hereinabove defined and R$^9$ is (1–4C)alkyl; or m is 2–4 and $R^6$ is hydroxy, (1–4C)alkanoylamino, amino, (1–4C)alkylamino, (1–4C)alkanesulphonamido, ureido, N$^3$-((1–4C)alkyl)ureido, di-(N$^3$-(1–4C)alkyl)ureido or of the formula —NHSO$_2$NR$^7$(R$^8$) wherein R$^7$ and R$^8$ are as hereinabove define;

and pharmaceutically-acceptable salts thereof.

2. A compound of the formula (I) as claimed in claim 1 wherein:

$R^1$ is of the formula —NHC(=O)(1–4C)alkyl;

one of $R^2$ and $R^3$ is hydrogen and the other is fluoro;

$R^4$ is hydrogen, methyl or oxo;

$R^5$ is (1–6C)alkyl or of the formula $R^6(CH_2)_m$— wherein either m is 1or 1and $R^6$ is trifluoromethyl, fluoromethyl, (1–4C)alkoxy, (1–4C)alkylS(O)$_p$— (wherein p is 0, 1 or 2), (1–4C)alkoxycarbonyl, carbamoyl, N-(1–4C)alkylcarbamoyl, or di-(N-(1–4C) alkyl)carbamoyl, or m is 2 or 3 and $R^6$ is hydroxy or (1–4C)alkanoylamino.

3. A compound of the formula (I) as claimed in claim 1 wherein:

$R^1$ is acetamido;

one of $R^2$ and $R^3$ is hydrogen and the other is fluoro;

$R^4$ is hydrogen, methyl or oxo;

$R^5$ is (1–6C)alkyl or of the formula $R^6(CH_2)_m$— wherein either m is 1 or 2 and $R^6$ is trifluoromethyl, fluoromethyl, (1–4C)alkoxy, (1–4C)alkylS(O)$_p$— (wherein p is 0, 1 or 2), (1–4C)alkoxycarbonyl, carbamoyl, N-(1–4C)alkylcarbamoyl, or di-(N-(1–4C) alkyl)carbamoyl, or m is 2 or 3 and $R^6$ is hydroxy or (1–4C)alkanoylamino.

4. A compound of the formula (I) as claimed in claim 1 wherein:

$R^1$ is acetamido;

one of $R^2$ and $R^3$ is hydrogen and the other is fluoro;

$R^4$ is hydrogen;

$R^5$ is (1–6C)alkyl or of the formula $R^6(CH_2)_m$— wherein either m is 1 or 2 and $R^6$ is trifluoromethyl, fluoromethyl, (1–4C)alkoxy, (1–4C)alkylS(O)$_p$— (wherein p is 0, 1 or 2), (1–4C)alkoxycarbonyl, carbamoyl, N-(1–4C)alkylcarbamoyl, or di-(N-(1–4C) alkyl)carbamoyl, or m is 2 or 3 and $R^6$ is hydroxy or (1–4C)alkanoylamino.

5. A compound of the formula (I) as claimed in claim 1 wherein:

$R^1$ is acetamido;

one of $R^2$ and $R^3$ is hydrogen and the other is fluoro;

$R^4$ is hydrogen;

$R^5$ is methyl, ethyl, 2, 2, 2-trifluoroethyl, 2-fluoroethyl, 2-methoxyethyl, methylthiomethyl, methoxycarbonylmethyl, carbamoylmethyl, di-(N-methyl)carbamoylmethyl, 2-hydroxyethyl or 2-(acetamido)ethyl.

6. A compound of the formula (I), or a pharmaceutically-acceptable salts thereof, as claimed in claim 1 selected from:

N-((5S)-3-(3-fluoro-4-(4-methyl-3-oxopiperazin-1-yl) phenyl)-2-oxooxazolidin-5-yl)methyl)acetamide;

N-((5S)-3-(3-fluoro-4-(4-ethyl-3-oxopiperazin-1-yl) phenyl)-2-oxooxazolidin-5-ylmethyl)acetamide;

N-((5S)-3-(3-fluoro-4-(4-(2-fluoroethyl)-3-oxopiperazin-1-yl)phenyl)-2-oxooxazolidin-5-ylmethyl)acetamide; and N-((5S)-3-(3-fluoro-4-(4-(2-methoxyethyl)-3-oxopiperazin-1-yl)phenyl)-2-oxooxazolidin-5-ylmethyl)acetamide.

7. A compound of the formula (I), or a pharmaceutically-acceptable salts thereof, as claimed in claim 1 being:

N-((5S)-3-(3-fluoro-4-(4-(2-fluoroethyl)-3-oxopiperazin-1-yl)phenyl)-2-oxooxazolidin-5-ylmethyl)acetamide.

8. A process for the preparation of a compound of the formula (I) as claimed in claim 1 which comprises:

(a) the deprotection a compound of the formula:

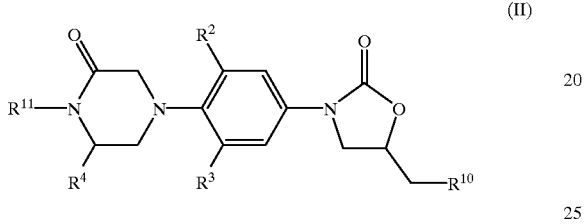

(II)

(c) when $R^1$ is of the formula —NHS(O)$_n$(1–4C)alkyl, wherein n is 1 or 2, the oxidation of a compound of the formula (I) wherein $R^1$ is —NHS(O)$_n$(1–4C)alkyl and n is 0 or, when n is 2 the oxidation of a compound of the formula (I) wherein $R^1$ is —NHS(O)$_n$(1–4C)alkyl and n is 1;

(d) when $R^1$ is of the formula —NHC(=O)(1–4C)alkyl or —NHS(O)(1–4C)alkyl, the reaction of a compound of the formula (III) with a compound of the formula (IV):

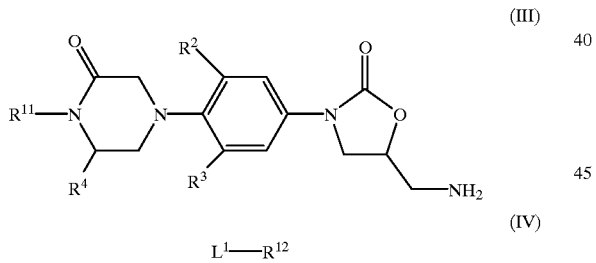

(III)

(IV)

$L^1$—$R^{12}$ (e) when $R^1$ is hydroxy, the reaction of a compound of the formula (V) with a compound of the formula (VI):

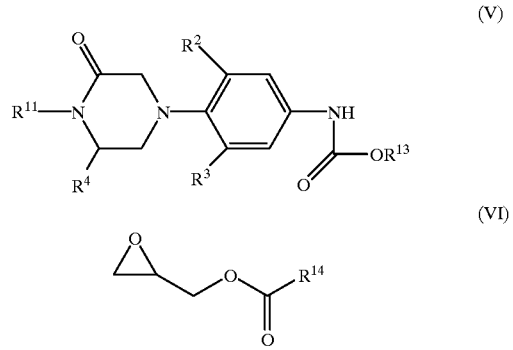

(V)

(VI)

(f) when $R^1$ is of the formula —NHC(=O)(1–4C)alkyl, the reaction of a compound of the formula (I) wherein $R^1$ is hydroxy with an amide of the formula (VII):

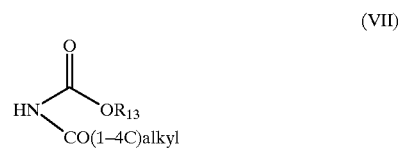

(VII)

wherein, in any of process routes (a)–(f), $R^2$, $R^3$, $R^4$ are as defined in claim 1; $R^{10}$ is $R^1$ or protected $R^1$, $R^{11}$ is $R^5$ or protected $R^5$ (wherein $R^1$ and $R^5$ are as defined hereinabove or in claim 1); $R^{12}$ is of the formula —C(=O)(1–4C)alkyl or —S(O)$_n$(1–4C)alkyl; $R^{13}$ is (1–6C)alkyl or benzyl; $R^{14}$ is (1–6C)alkyl and $L^1$ is a leaving group; and thereafter:

i) removing any protecting groups present; and ii) optionally forming a pharmaceutically-acceptable salt, and optionally obtaining an optically active form of a compound of the formula (I) by carrying out one of the above procedures using an optically active starting material or intermediate.

9. A pharmaceutical composition which comprises a compound of the formula (I) or a pharmaceutically-acceptable salt thereof, as claimed in any of claims 1 and 2 to 7 and a pharmaceutically-acceptable diluent or carrier.

10. A method for producing an antibacterial effect in a warm blooded animal in need thereof, said method comprising administering to said animal an antibacterially effective amount of a compound of the formula (I), or a pharmaceutically-acceptable salt thereof, as claimed in any one of claims 1 and 2 to 7.

* * * * *